United States Patent
Hong

(10) Patent No.: US 11,998,798 B2
(45) Date of Patent: Jun. 4, 2024

(54) VIRTUAL GUIDED FITNESS ROUTINES FOR AUGMENTED REALITY EXPERIENCES

(71) Applicant: Megan Hong, Playa Vista, CA (US)

(72) Inventor: Megan Hong, Playa Vista, CA (US)

(73) Assignee: Snap Inc., Santa Monica, CA (US)

(*) Notice: Subject to any disclaimer, the term of this patent is extended or adjusted under 35 U.S.C. 154(b) by 212 days.

(21) Appl. No.: 17/321,178

(22) Filed: May 14, 2021

(65) Prior Publication Data

US 2022/0362631 A1    Nov. 17, 2022

(51) Int. Cl.
| | |
|---|---|
| *G09G 5/00* | (2006.01) |
| *A63B 24/00* | (2006.01) |
| *A63B 71/06* | (2006.01) |
| *G06F 3/0488* | (2022.01) |

(52) U.S. Cl.
CPC ...... *A63B 24/0006* (2013.01); *A63B 24/0087* (2013.01); *A63B 71/0622* (2013.01); *G06F 3/0488* (2013.01); *A63B 2024/0015* (2013.01); *A63B 2024/0096* (2013.01); *A63B 2071/063* (2013.01); *A63B 2071/0638* (2013.01); *A63B 2071/0666* (2013.01); *A63B 2071/068* (2013.01); *A63B 2220/17* (2013.01); *A63B 2220/806* (2013.01)

(58) Field of Classification Search
CPC ....... G06T 19/006; G06T 19/00; G06F 3/011; G06F 3/012; G02B 27/017
USPC ......................................................... 345/633
See application file for complete search history.

(56) References Cited

U.S. PATENT DOCUMENTS

| | | | |
|---|---|---|---|
| 11,145,126 B1* | 10/2021 | Bramwell | ............... G06F 3/147 |
| 2013/0095924 A1 | 4/2013 | Geisner et al. | |
| 2017/0266551 A1 | 9/2017 | Baba | |
| 2018/0121728 A1* | 5/2018 | Wells | ..................... G06V 40/23 |
| 2019/0160339 A1 | 5/2019 | Zhang et al. | |
| 2019/0311539 A1* | 10/2019 | Hogue | ............... G02B 27/0172 |
| 2020/0104039 A1 | 4/2020 | Robertson et al. | |
| 2021/0008413 A1* | 1/2021 | Asikainen | ............. G06F 3/0304 |

(Continued)

OTHER PUBLICATIONS

International Search Report and Written Opinion for International Application No. PCT/US2022/028515, dated Aug. 4, 2022 (dated Aug. 4, 2022)—11 pages.

*Primary Examiner* — Gordon G Liu
(74) *Attorney, Agent, or Firm* — Culhane PLLC; Stephen J. Weed

(57) ABSTRACT

Example systems, devices, media, and methods are described for presenting a virtual guided fitness experience using the display of an eyewear device in augmented reality. A guided fitness application implements and controls the capturing of frames of motion data using an inertial measurement unit (IMU) and video data from one or more cameras. The method includes detecting exercise motions (with or without equipment) as well as detecting and counting repetitions. Relevant data about detected motions or equipment is retrieved and used to curate the guided fitness experience. A current rep count is presented on the display along with an avatar for playing messages, performing animated demonstrations, responding to commands and queries using speech recognition, and presenting guided fitness instructions through text, audio, and video.

20 Claims, 17 Drawing Sheets

(56) References Cited

U.S. PATENT DOCUMENTS

2021/0072947 A1 3/2021 Anderson et al.
2022/0245880 A1 8/2022 Thielen et al.

* cited by examiner

US 11,998,798 B2

VIRTUAL GUIDED FITNESS ROUTINES FOR AUGMENTED REALITY EXPERIENCES

TECHNICAL FIELD

Examples set forth in the present disclosure relate to the field of augmented reality experiences for electronic devices, including wearable devices such as eyewear. More particularly, but not by way of limitation, the present disclosure describes the presentation of virtual guided exercises and fitness routines in augmented reality.

BACKGROUND

Many types of computers and electronic devices available today, such as mobile devices (e.g., smartphones, tablets, and laptops), handheld devices, and wearable devices (e.g., smart glasses, digital eyewear, headwear, headgear, and head-mounted displays), include a variety of cameras, sensors, wireless transceivers, input systems, and displays.

Virtual reality (VR) technology generates a complete virtual environment including realistic images, sometimes presented on a VR headset or other head-mounted display. VR experiences allow a user to move through the virtual environment and interact with virtual objects. Augmented reality (AR) is a type of VR technology that combines real objects in a physical environment with virtual objects and displays the combination to a user. The combined display gives the impression that the virtual objects are authentically present in the environment, especially when the virtual objects appear and behave like the real objects. Cross reality (XR) is generally understood as an umbrella term referring to systems that include or combine elements from AR, VR, and MR (mixed reality) environments.

Graphical user interfaces allow the user to interact with displayed content, including virtual objects and graphical elements such as icons, taskbars, list boxes, menus, buttons, and selection control elements like cursors, pointers, handles, and sliders.

Automatic speech recognition (ASR) is a field of computer science, artificial intelligence, and linguistics which involves receiving spoken words and converting the spoken words into audio data suitable for processing by a computing device. Processed frames of audio data can be used to translate the received spoken words into text or to convert the spoken words into commands for controlling and interacting with various software applications. ASR processing may be used by computers, handheld devices, wearable devices, telephone systems, automobiles, and a wide variety of other devices to facilitate human-computer interactions.

BRIEF DESCRIPTION OF THE DRAWINGS

Features of the various examples described will be readily understood from the following detailed description, in which reference is made to the figures. A reference numeral is used with each element in the description and throughout the several views of the drawing. When a plurality of similar elements is present, a single reference numeral may be assigned to like elements, with an added lower-case letter referring to a specific element.

The various elements shown in the figures are not drawn to scale unless otherwise indicated. The dimensions of the various elements may be enlarged or reduced in the interest of clarity. The several figures depict one or more implementations and are presented by way of example only and should not be construed as limiting. Included in the drawing are the following figures.

DETAILED DESCRIPTION

Figure 1A:
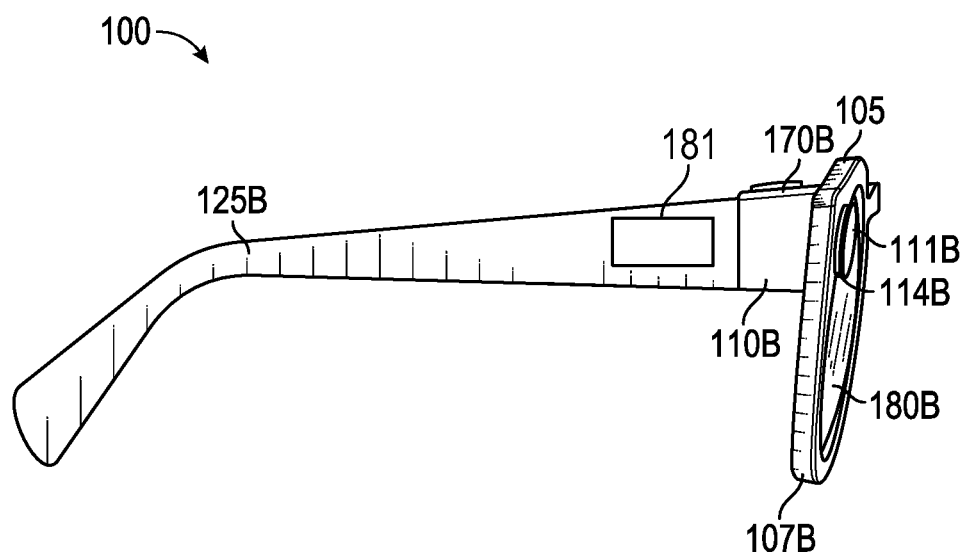
FIG. 1A is a side view (right) of an example hardware configuration of an eyewear device suitable for use in an example virtual guided fitness system.

Various implementations and details are described with reference to examples for presenting a virtual fitness experience in augmented reality. For example, an exercise motion or apparatus is detected using motion data captured by an inertial measurement unit (IMU) and image data captured by a camera. Relevant data about the detected motion or apparatus is retrieved from libraries and internet searches. The virtual fitness experience includes presenting a repetitions counter on the display along with an avatar for playing messages and animated tutorials.

Example methods include starting a virtual fitness experience in response to detecting an exercise motion in a physical environment with an eyewear device. The eyewear device includes an IMU, a camera system, a microphone, a loudspeaker, a guided fitness application, an image processing system, and a display. The method includes capturing frames of motion data with the inertial measurement unit and then, detecting a device motion (e.g., motion of the eyewear device, supported by the wearer) within the captured frames of motion data. Analysis of the detected device motion includes determining whether the detected device motion matches a first predefined exercise activity from among a plurality of predefined exercise activities stored in an activity library. In response to a match, the guided fitness application retrieves exercise data associated with the first predefined exercise activity and presents on the display the virtual fitness experience, which is based on the retrieved exercise data.

The process of presenting a virtual fitness experience includes presenting an avatar on the display, playing (through the avatar) one or more messages and lectures associated with the retrieved exercise data. The process of playing through the avatar includes presenting text in a text bubble, playing audio messages through the loudspeaker, presenting a video on the display, or combinations there. The process also includes animating the avatar to perform a demonstration on the display in correlation with a lesson.

The process of presenting a virtual fitness experience also includes detecting a repetitive motion (e.g., motion of the device, supported by the wearer) within the captured frames of motion data. If the detected repetitive motion matches a first predefined repetition activity, then the guided fitness application increments a current rep count on the display. The process in some implementations includes detecting an exercise apparatus (e.g., a dumbbell) and detecting a repetitive apparatus motion (e.g., a dumbbell performing a bicep curl). If the detected repetitive apparatus motion matches a first predefined apparatus repetition activity, then the guided fitness application increments a current rep count on the display. The messages may include a closing message reporting the actual duration of the exercise program or session, the number of repetitions completed, the number of calories burned, and the like.

Although the various systems and methods are described herein with reference to fitness, exercises, and exercise equipment, the technology described may be applied to detecting any type of experience or activity occurring in a physical environment, retrieving data about the detected activity, and presenting a virtual guided tutorial, lesson, training, teaching, or other guidance on a display.

The following detailed description includes systems, methods, techniques, instruction sequences, and computing machine program products illustrative of examples set forth in the disclosure. Numerous details and examples are included for the purpose of providing a thorough understanding of the disclosed subject matter and its relevant teachings. Those skilled in the relevant art, however, may understand how to apply the relevant teachings without such details. Aspects of the disclosed subject matter are not limited to the specific devices, systems, and method described because the relevant teachings can be applied or practice in a variety of ways. The terminology and nomenclature used herein is for the purpose of describing particular aspects only and is not intended to be limiting. In general, well-known instruction instances, protocols, structures, and techniques are not necessarily shown in detail.

The terms "coupled" or "connected" as used herein refer to any logical, optical, physical, or electrical connection, including a link or the like by which the electrical or magnetic signals produced or supplied by one system element are imparted to another coupled or connected system element. Unless described otherwise, coupled or connected elements or devices are not necessarily directly connected to one another and may be separated by intermediate components, elements, or communication media, one or more of which may modify, manipulate, or carry the electrical signals. The term "on" means directly supported by an element or indirectly supported by the element through another element that is integrated into or supported by the element.

The term "proximal" is used to describe an item or part of an item that is situated near, adjacent, or next to an object or person; or that is closer relative to other parts of the item, which may be described as "distal." For example, the end of an item nearest an object may be referred to as the proximal end, whereas the generally opposing end may be referred to as the distal end.

The orientations of the eyewear device, other mobile devices, coupled components, and any other devices such as those shown in any of the drawings, are given by way of example only, for illustration and discussion purposes. In operation, the eyewear device may be oriented in any other direction suitable to the particular application of the eyewear device; for example, up, down, sideways, or any other orientation. Also, to the extent used herein, any directional term, such as front, rear, inward, outward, toward, left, right, lateral, longitudinal, up, down, upper, lower, top, bottom, side, horizontal, vertical, and diagonal are used by way of example only, and are not limiting as to the direction or orientation of any camera, inertial measurement unit, or display as constructed or as otherwise described herein.

Advanced AR technologies, such as computer vision and object tracking, may be used to produce a perceptually enriched and immersive experience. Computer vision algorithms extract three-dimensional data about the physical world from the data captured in digital images or video. Object recognition and tracking algorithms are used to detect an object in a digital image or video, estimate its orientation or pose, and track its movement over time. Hand and finger recognition and tracking in real time is one of the most challenging and processing-intensive tasks in the field of computer vision.

The term "pose" refers to the static position and orientation of an object at a particular instant in time. The term "gesture" refers to the active movement of an object, such as a hand, through a series of poses, sometimes to convey a signal or idea. The terms, pose and gesture, are sometimes used interchangeably in the field of computer vision and augmented reality. As used herein, the terms "pose" or "gesture" (or variations thereof) are intended to be inclusive of both poses and gestures; in other words, the use of one term does not exclude the other.

Additional objects, advantages and novel features of the examples will be set forth in part in the following description, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

Reference now is made in detail to the examples illustrated in the accompanying drawings and discussed below.

FIG. 1A is a side view (right) of an example hardware configuration of an eyewear device 100 which includes a touch-sensitive input device such as a touchpad 181. As shown, the touchpad 181 may have a boundary that is plainly visible or include a raised or otherwise tactile edge that provides feedback to the user about the location and boundary of the touchpad 181; alternatively, the boundary may be subtle and not easily seen or felt. In other implementations, the eyewear device 100 may include a touchpad 181 on the left side that operates independently or in conjunction with a touchpad 181 on the right side.

The surface of the touchpad 181 is configured to detect finger touches, taps, and gestures (e.g., moving touches) for use with a GUI displayed by the eyewear device, on an image display, to allow the user to navigate through and select menu options in an intuitive manner, which enhances and simplifies the user experience.

Detection of finger inputs on the touchpad 181 can enable several functions. For example, touching anywhere on the touchpad 181 may cause the GUI to display or highlight an item on the image display, which may be projected onto at least one of the optical assemblies 180A, 180B. Tapping or double tapping on the touchpad 181 may select an item or icon. Sliding or swiping a finger in a particular direction (e.g., from front to back, back to front, up to down, or down to) may cause the items or icons to slide or scroll in a particular direction; for example, to move to a next item, icon, video, image, page, or slide. Sliding the finger in another direction may slide or scroll in the opposite direction; for example, to move to a previous item, icon, video, image, page, or slide. The touchpad 181 can be virtually anywhere on the eyewear device 100.

In one example, an identified finger gesture of a single tap on the touchpad 181, initiates selection or pressing of a graphical user interface element in the image presented on the image display of the optical assembly 180A, 180B. An adjustment to the image presented on the image display of the optical assembly 180A, 180B based on the identified finger gesture can be a primary action which selects or submits the graphical user interface element on the image display of the optical assembly 180A, 180B for further display or execution.

As shown, the eyewear device 100 includes a right visible-light camera 114B. As further described herein, two cameras 114A, 114B capture image information for a scene from two separate viewpoints. The two captured images may be used to project a three-dimensional display onto an image display for viewing with 3D glasses.

Figure 1B:
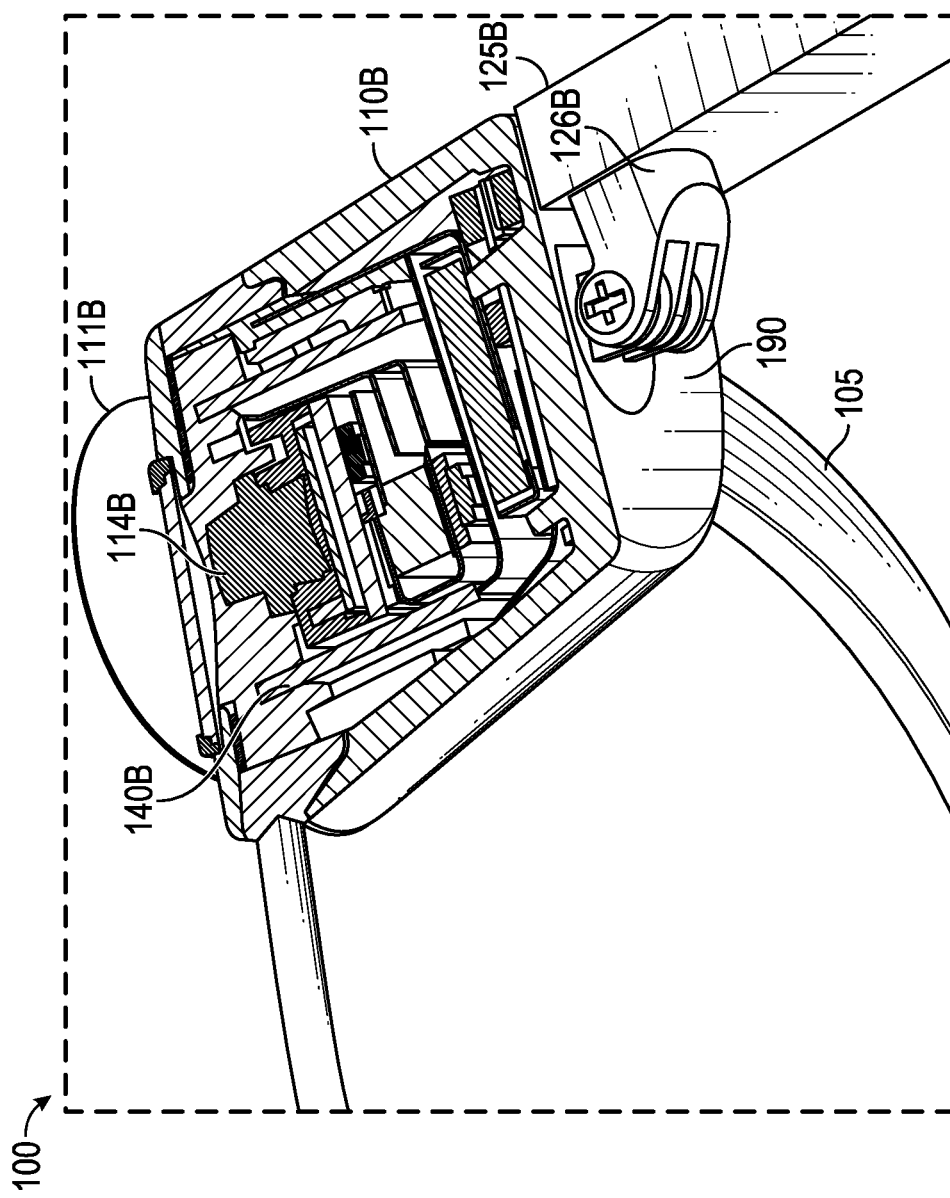
FIG. 1B is a perspective, partly sectional view of a right corner of the eyewear device of FIG. 1A depicting a right visible-light camera, and a circuit board.
Figure 1C:
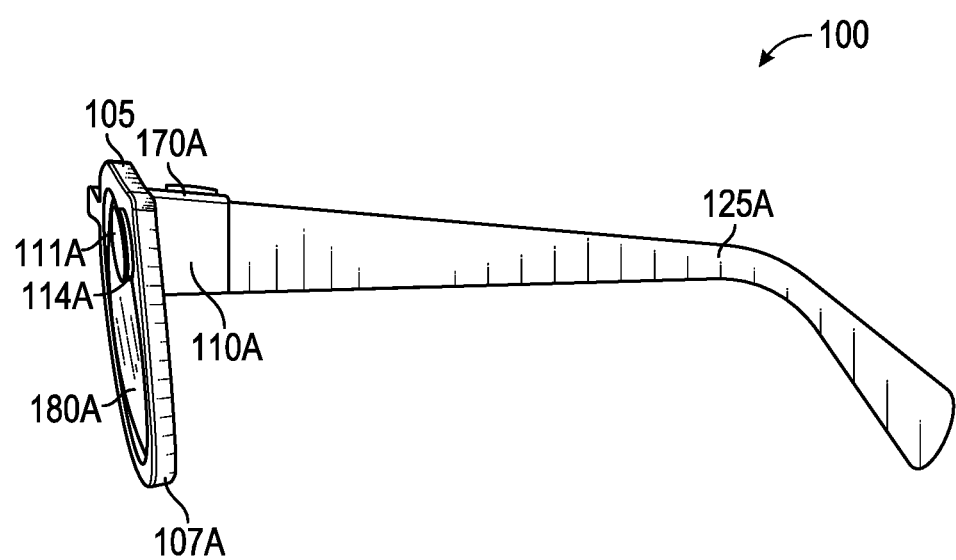
FIG. 1C is a side view (left) of an example hardware configuration of the eyewear device of FIG. 1A, which shows a left visible-light camera.
Figure 1D:
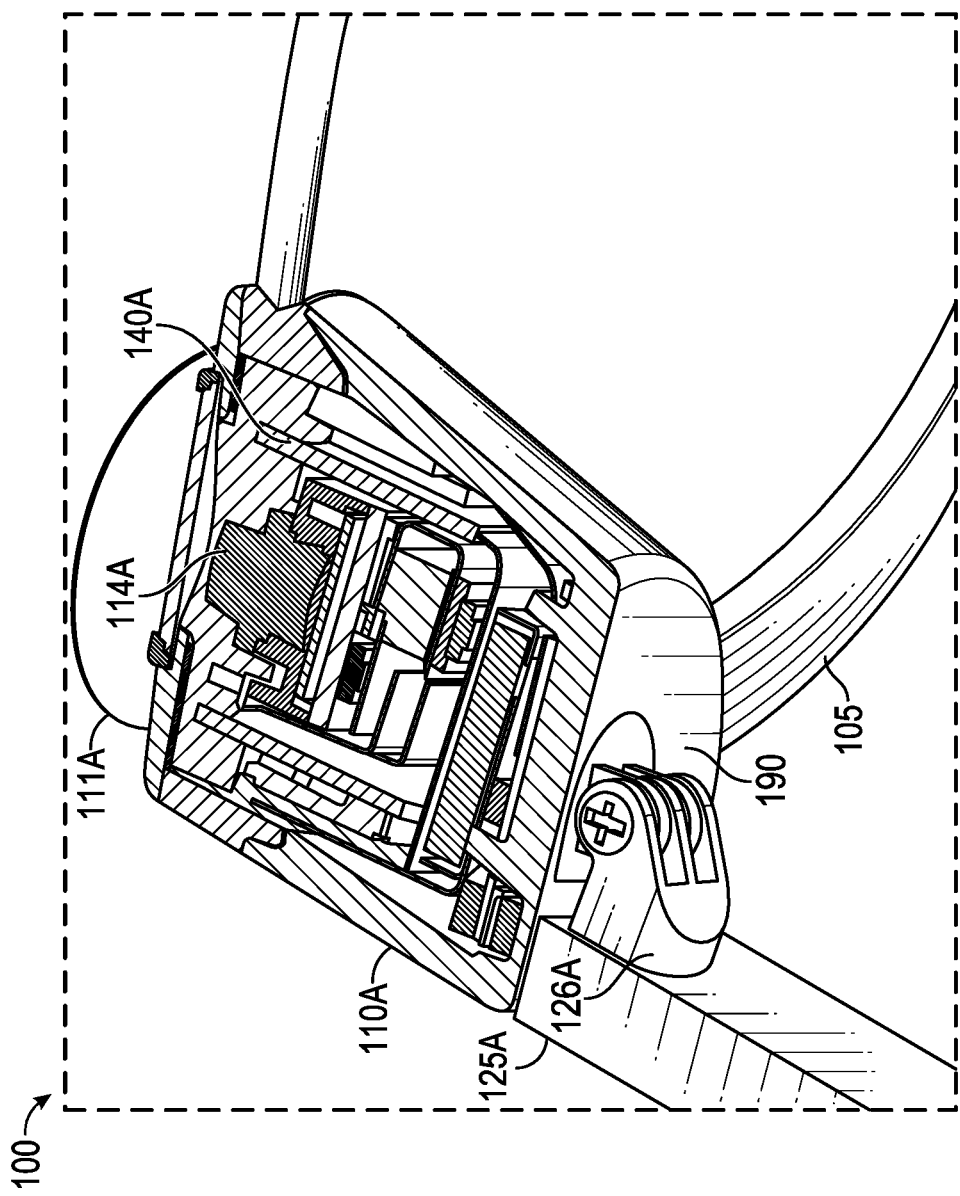
FIG. 1D is a perspective, partly sectional view of a left corner of the eyewear device of FIG. 1C depicting the left visible-light camera, and a circuit board.

The eyewear device 100 includes a right optical assembly 180B with an image display to present images, such as depth images. As shown in FIGS. 1A and 1B, the eyewear device 100 includes the right visible-light camera 114B. The eyewear device 100 can include multiple visible-light cameras 114A, 114B that form a passive type of three-dimensional camera, such as stereo camera, of which the right visible-light camera 114B is located on a right corner 110B. As shown in FIGS. 1C-D, the eyewear device 100 also includes a left visible-light camera 114A.

Figure 3:
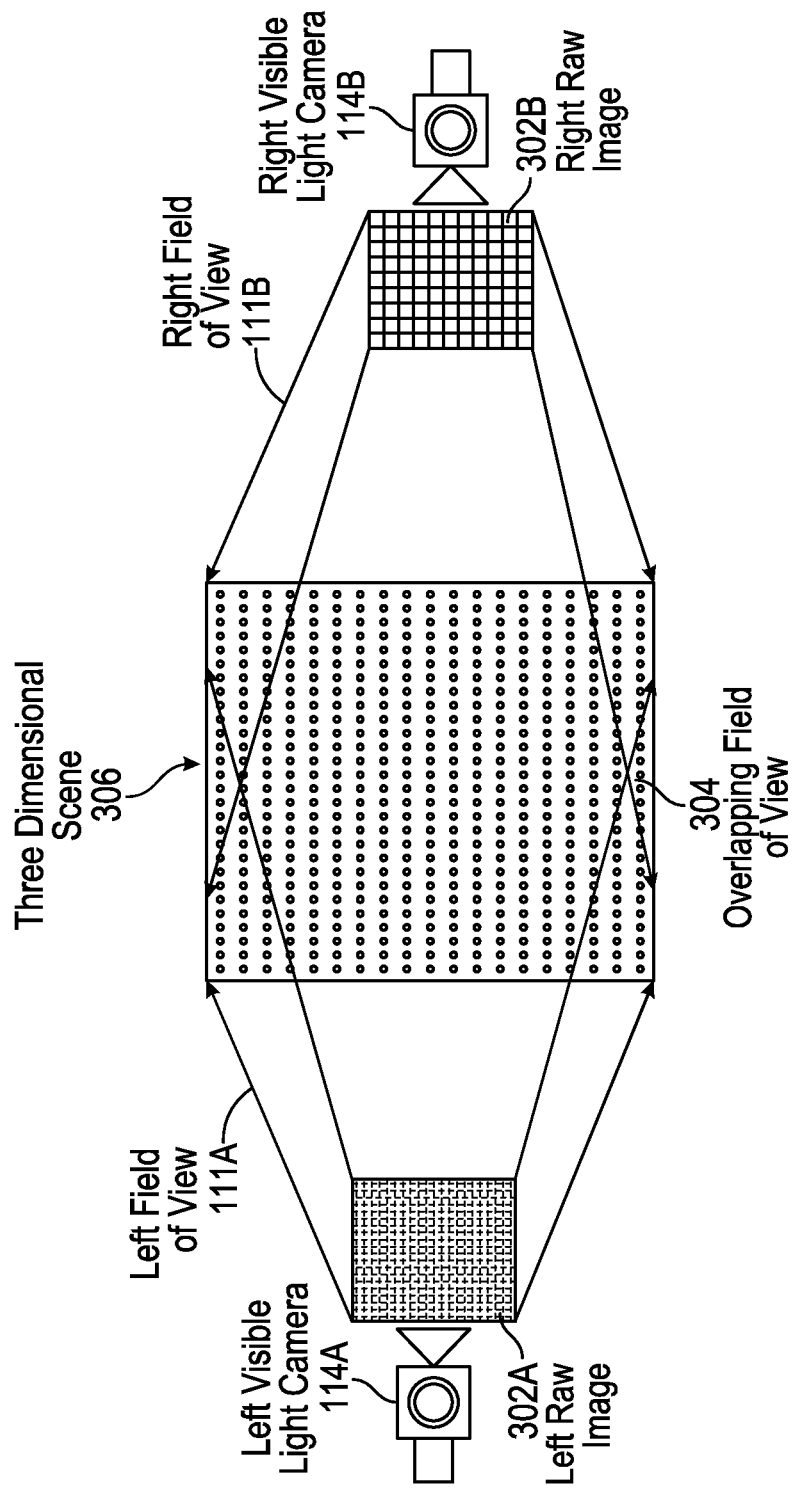
FIG. 3 is a diagrammatic depiction of a three-dimensional scene, a left raw image captured by a left visible-light camera, and a right raw image captured by a right visible-light camera.

Left and right visible-light cameras 114A, 114B are sensitive to the visible-light range wavelength. Each of the visible-light cameras 114A, 114B have a different frontward facing field of view which are overlapping to enable generation of three-dimensional depth images, for example, right visible-light camera 114B depicts a right field of view 111B. Generally, a "field of view" is the part of the scene that is visible through the camera at a particular position and orientation in space. The fields of view 111A and 111B have an overlapping field of view 304 (FIG. 3). Objects or object features outside the field of view 111A, 111B when the visible-light camera captures the image are not recorded in a raw image (e.g., photograph or picture). The field of view describes an angle range or extent, which the image sensor of the visible-light camera 114A, 114B picks up electromagnetic radiation of a given scene in a captured image of the given scene. Field of view can be expressed as the angular size of the view cone; i.e., an angle of view. The angle of view can be measured horizontally, vertically, or diagonally.

In an example configuration, one or both visible-light cameras 114A, 114B has a field of view of 100° and a resolution of 480×480 pixels. The "angle of coverage" describes the angle range that a lens of visible-light cameras 114A, 114B or infrared camera 410 (see FIG. 2A) can effectively image. Typically, the camera lens produces an image circle that is large enough to cover the film or sensor of the camera completely, possibly including some vignetting (e.g., a darkening of the image toward the edges when compared to the center). If the angle of coverage of the camera lens does not fill the sensor, the image circle will be visible, typically with strong vignetting toward the edge, and the effective angle of view will be limited to the angle of coverage.

Examples of such visible-light cameras 114A, 114B include a high-resolution complementary metal-oxide-semiconductor (CMOS) image sensor and a digital VGA camera (video graphics array) capable of resolutions of 480p (e.g., 640×480 pixels), 720p, 1080p, or greater. Other examples include visible-light cameras 114A, 114B that can capture high-definition (HD) video at a high frame rate (e.g., thirty to sixty frames per second, or more) and store the recording at a resolution of 1216 by 1216 pixels (or greater).

The eyewear device 100 may capture image sensor data from the visible-light cameras 114A, 114B along with geolocation data, digitized by an image processor, for storage in a memory. The visible-light cameras 114A, 114B capture respective left and right raw images in the two-dimensional space domain that comprise a matrix of pixels on a two-dimensional coordinate system that includes an X-axis for horizontal position and a Y-axis for vertical position. Each pixel includes a color attribute value (e.g., a red pixel light value, a green pixel light value, or a blue pixel light value); and a position attribute (e.g., an X-axis coordinate and a Y-axis coordinate).

In order to capture stereo images for later display as a three-dimensional projection, the image processor 412 (shown in FIG. 4) may be coupled to the visible-light cameras 114A, 114B to receive and store the visual image information. The image processor 412, or another processor, controls operation of the visible-light cameras 114A, 114B to act as a stereo camera simulating human binocular vision and may add a timestamp to each image. The timestamp on each pair of images allows display of the images together as part of a three-dimensional projection. Three-dimensional projections produce an immersive, life-like experience that is desirable in a variety of contexts, including virtual reality (VR) and video gaming.

FIG. 1B is a perspective, cross-sectional view of a right corner 110B of the eyewear device 100 of FIG. 1A depicting the right visible-light camera 114B of the camera system, and a circuit board. FIG. 1C is a side view (left) of an example hardware configuration of an eyewear device 100 of FIG. 1A, which shows a left visible-light camera 114A of the camera system. FIG. 1D is a perspective, cross-sectional view of a left corner 110A of the eyewear device of FIG. 1C depicting the left visible-light camera 114A of the three-dimensional camera, and a circuit board.

Construction and placement of the left visible-light camera 114A is substantially similar to the right visible-light camera 114B, except the connections and coupling are on the left lateral side 170A. As shown in the example of FIG. 1B, the eyewear device 100 includes the right visible-light camera 114B and a circuit board 140B, which may be a flexible printed circuit board (PCB). A right hinge 126B connects the right corner 110B to a right temple 125B of the eyewear device 100. In some examples, components of the right visible-light camera 114B, the flexible PCB 140B, or other electrical connectors or contacts may be located on the right temple 125B or the right hinge 126B. A left hinge 126B connects the left corner 110A to a left temple 125A of the eyewear device 100. In some examples, components of the left visible-light camera 114A, the flexible PCB 140A, or other electrical connectors or contacts may be located on the left temple 125A or the left hinge 126A.

The right corner 110B includes corner body 190 and a corner cap, with the corner cap omitted in the cross-section of FIG. 1B. Disposed inside the right corner 110B are various interconnected circuit boards, such as PCBs or flexible PCBs, that include controller circuits for right visible-light camera 114B, microphone(s) 139, loudspeaker(s) 191, low-power wireless circuitry (e.g., for wireless short range network communication via Bluetooth™), high-speed wireless circuitry (e.g., for wireless local area network communication via Wi-Fi).

Figure 2A:
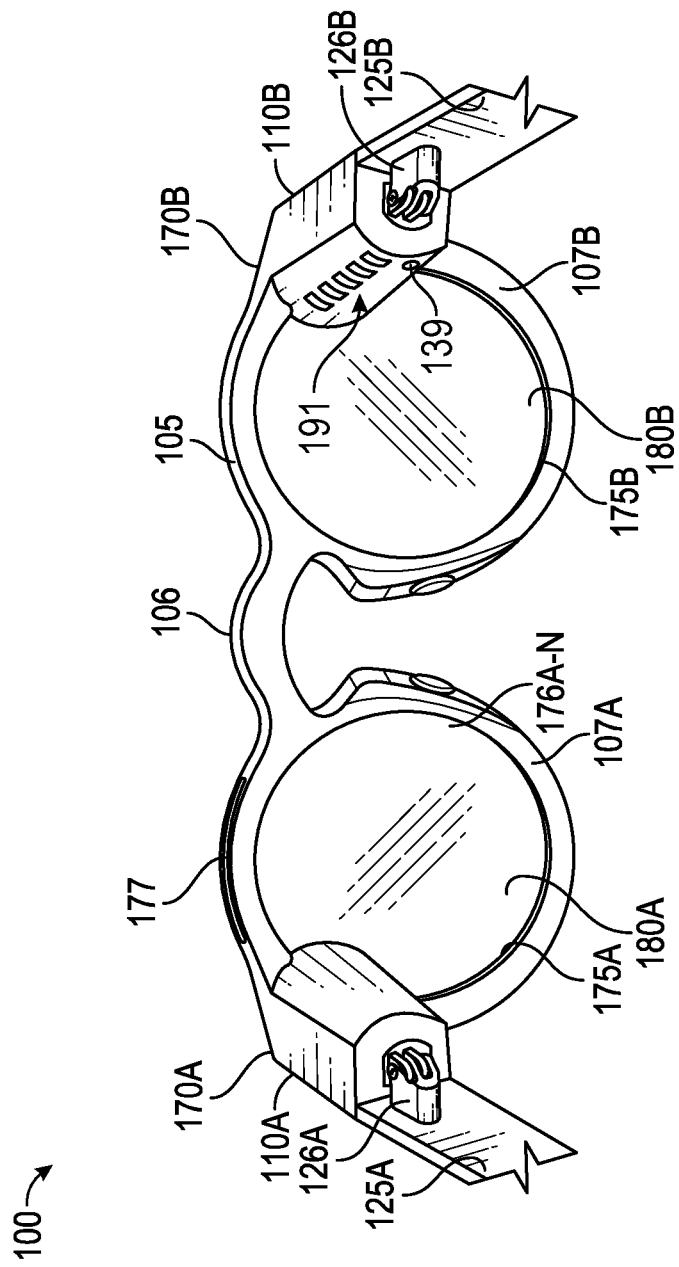
FIGS. 2A and 2B are rear views of example hardware configurations of an eyewear device utilized in an example virtual guided fitness system.

The right visible-light camera 114B is coupled to or disposed on the flexible PCB 140B and covered by a visible-light camera cover lens, which is aimed through opening(s) formed in the frame 105. For example, the right rim 107B of the frame 105, shown in FIG. 2A, is connected to the right corner 110B and includes the opening(s) for the visible-light camera cover lens. The frame 105 includes a front side configured to face outward and away from the eye of the user. The opening for the visible-light camera cover lens is formed on and through the front or outward-facing side of the frame 105. In the example, the right visible-light camera 114B has an outward-facing field of view 111B (shown in FIG. 3) with a line of sight or perspective that is correlated with the right eye of the user of the eyewear device 100. The visible-light camera cover lens can also be adhered to a front side or outward-facing surface of the right corner 110B in which an opening is formed with an outward-facing angle of coverage, but in a different outwardly direction. The coupling can also be indirect via intervening components.

As shown in FIG. 1B, flexible PCB 140B is disposed inside the right corner 110B and is coupled to one or more other components housed in the right corner 110B. Although shown as being formed on the circuit boards of the right corner 110B, the right visible-light camera 114B can be formed on the circuit boards of the left corner 110A, the temples 125A, 125B, or the frame 105.

Figure 2B:
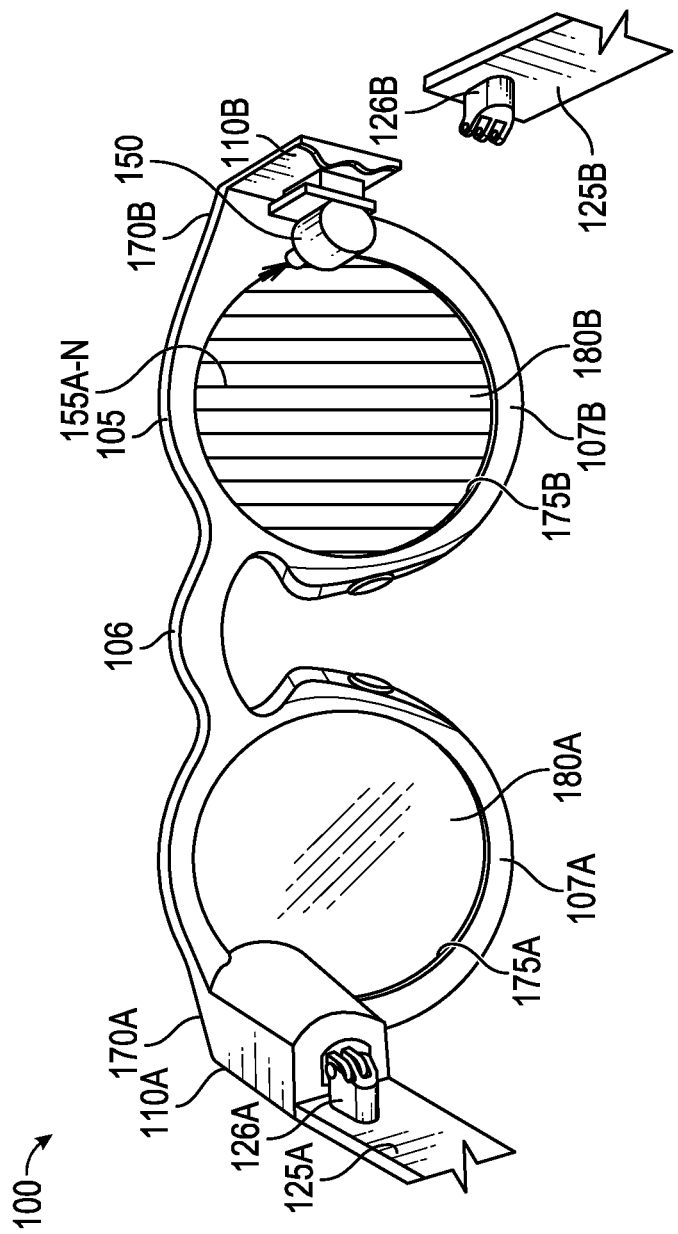

FIGS. 2A and 2B are perspective views, from the rear, of example hardware configurations of the eyewear device 100, including two different types of image displays. The eyewear device 100 is sized and shaped in a form configured for wearing by a user; the form of eyeglasses is shown in the example. The eyewear device 100 can take other forms and may incorporate other types of frameworks; for example, a headgear, a headset, or a helmet.

In the eyeglasses example, eyewear device 100 includes a frame 105 including a left rim 107A connected to a right rim 107B via a bridge 106 adapted to be supported by a nose of the user. The left and right rims 107A, 107B include respective apertures 175A, 175B, which hold a respective optical element 180A, 180B, such as a lens and a display device. As used herein, the term "lens" is meant to include transparent or translucent pieces of glass or plastic having curved or flat surfaces that cause light to converge or diverge or that cause little or no convergence or divergence.

FIG. 2A is an example hardware configuration for the eyewear device 100 in which the right corner 110B supports a microphone 139 and a loudspeaker 191. The microphone 139 includes a transducer that converts sound into a corresponding electrical audio signal. The microphone 139 in this example, as shown, is positioned with an opening that faces inward toward the wearer, to facilitate reception of the sound waves, such as human speech including verbal commands and questions. Additional or differently oriented openings may be implemented. In other example configurations, the eyewear device 100 is coupled to one or more microphones 139, configured to operate together or independently, and positioned at various locations on the eyewear device 100.

Figure 4:
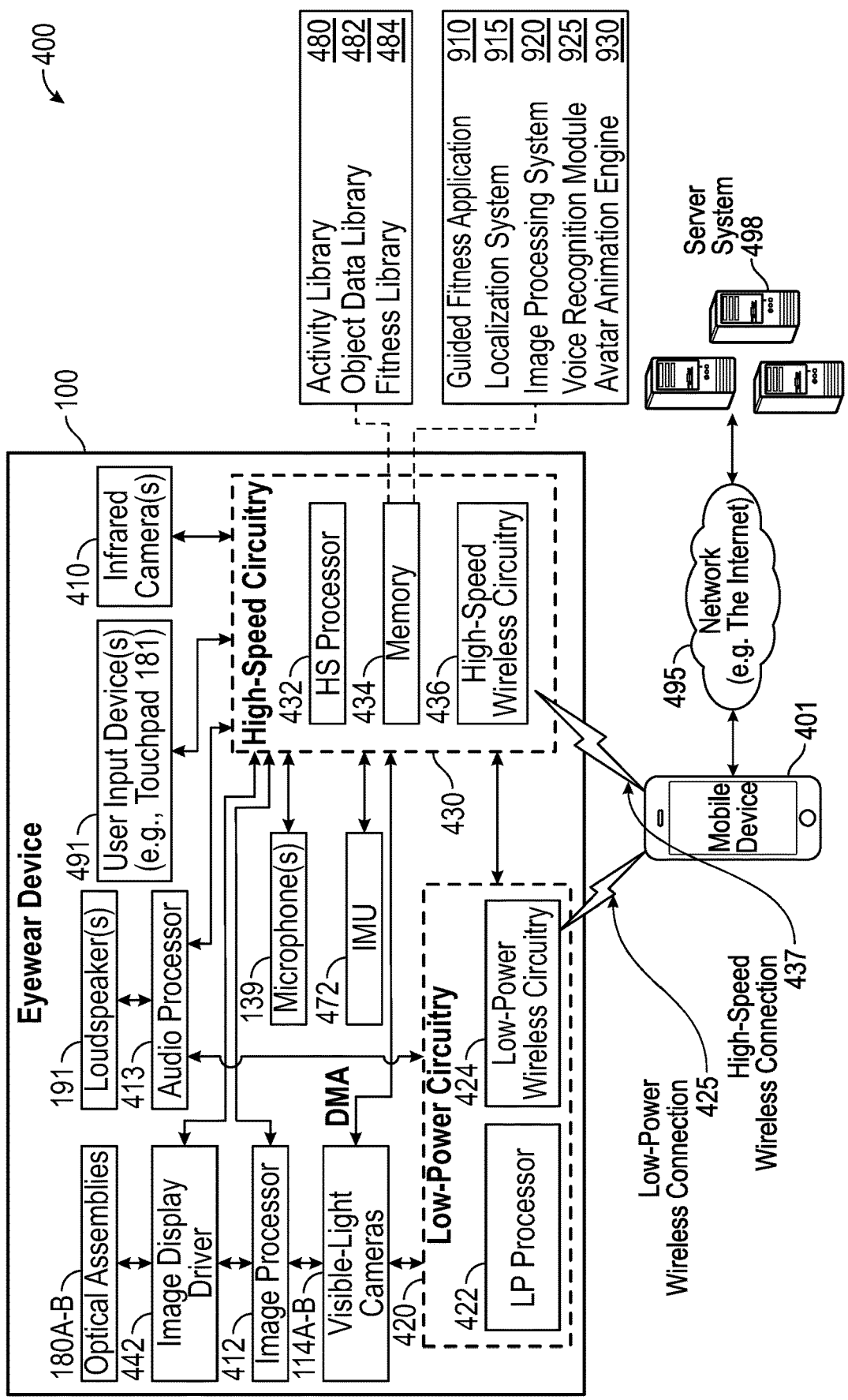
FIG. 4 is a functional block diagram of an example virtual guided fitness system including an eyewear device and a server system connected via various networks.

The loudspeaker 191 includes an electro-acoustic transducer that converts an electrical audio signal into a corresponding sound. The loudspeaker 191 is controlled by one of the processors 422, 432 or by an audio processor 413 (FIG. 4). The loudspeaker 191 in this example includes a series of oblong apertures, as shown, that face inward to direct the sound toward the wearer. Additional or differently oriented apertures may be implemented. In other example configurations, the eyewear device 100 is coupled to one or more loudspeakers 191, configured to operate together (e.g., in stereo, in zones to generate surround sound) or independently, and positioned at various locations on the eyewear device 100. For example, one or more loudspeakers 191 may be incorporated into the frame 105, temples 125, or corners 110A, 110B of the eyewear device 100.

Although shown in FIG. 2A and FIG. 2B as having two optical elements 180A, 180B, the eyewear device 100 can include other arrangements, such as a single optical element (or it may not include any optical element 180A, 180B), depending on the application or the intended user of the eyewear device 100. As further shown, eyewear device 100 includes a left corner 110A adjacent the left lateral side 170A of the frame 105 and a right corner 110B adjacent the right lateral side 170B of the frame 105. The corners 110A, 110B may be integrated into the frame 105 on the respective sides 170A, 170B (as illustrated) or implemented as separate components attached to the frame 105 on the respective sides 170A, 170B. Alternatively, the corners 110A, 110B may be integrated into temples (not shown) attached to the frame 105.

In one example, the image display of optical assembly 180A, 180B includes an integrated image display. As shown in FIG. 2A, each optical assembly 180A, 180B includes a suitable display matrix 177, such as a liquid crystal display (LCD), an organic light-emitting diode (OLED) display, or any other such display. Each optical assembly 180A, 180B also includes an optical layer or layers 176, which can include lenses, optical coatings, prisms, mirrors, waveguides, optical strips, and other optical components in any combination. The optical layers 176A, 176B, . . . 176N (shown as 176A-N in FIG. 2A and herein) can include a prism having a suitable size and configuration and including a first surface for receiving light from a display matrix and a second surface for emitting light to the eye of the user. The prism of the optical layers 176A-N extends over all or at least a portion of the respective apertures 175A, 175B formed in the left and right rims 107A, 107B to permit the user to see the second surface of the prism when the eye of the user is viewing through the corresponding left and right rims 107A, 107B. The first surface of the prism of the optical layers 176A-N faces upwardly from the frame 105 and the display matrix 177 overlies the prism so that photons and light emitted by the display matrix 177 impinge the first surface. The prism is sized and shaped so that the light is refracted within the prism and is directed toward the eye of the user by the second surface of the prism of the optical layers 176A-N. In this regard, the second surface of the prism of the optical layers 176A-N can be convex to direct the light toward the center of the eye. The prism can optionally be sized and shaped to magnify the image projected by the display matrix 177, and the light travels through the prism so that the image viewed from the second surface is larger in one or more dimensions than the image emitted from the display matrix 177.

In one example, the optical layers 176A-N may include an LCD layer that is transparent (keeping the lens open) unless and until a voltage is applied which makes the layer opaque (closing or blocking the lens). The image processor 412 on the eyewear device 100 may execute programming to apply the voltage to the LCD layer in order to produce an active shutter system, making the eyewear device 100 suitable for viewing visual content when displayed as a three-dimensional projection. Technologies other than LCD may be used for the active shutter mode, including other types of reactive layers that are responsive to a voltage or another type of input.

In another example, the image display device of optical assembly 180A, 180B includes a projection image display as shown in FIG. 2B. Each optical assembly 180A, 180B includes a laser projector 150, which is a three-color laser projector using a scanning mirror or galvanometer. During operation, an optical source such as a laser projector 150 is disposed in or on one of the temples 125A, 125B of the eyewear device 100. Optical assembly 180B in this example includes one or more optical strips 155A, 155B, . . . 155N (shown as 155A-N in FIG. 2B) which are spaced apart and across the width of the lens of each optical assembly 180A, 180B or across a depth of the lens between the front surface and the rear surface of the lens.

As the photons projected by the laser projector 150 travel across the lens of each optical assembly 180A, 180B, the photons encounter the optical strips 155A-N. When a particular photon encounters a particular optical strip, the photon is either redirected toward the user's eye, or it passes to the next optical strip. A combination of modulation of laser projector 150, and modulation of optical strips, may control specific photons or beams of light. In an example, a processor controls optical strips 155A-N by initiating mechanical, acoustic, or electromagnetic signals. Although shown as having two optical assemblies 180A, 180B, the eyewear device 100 can include other arrangements, such as a single or three optical assemblies, or each optical assembly 180A, 180B may have arranged different arrangement depending on the application or intended user of the eyewear device 100.

As further shown in FIGS. 2A and 2B, eyewear device 100 includes a left corner 110A adjacent the left lateral side 170A of the frame 105 and a right corner 110B adjacent the right lateral side 170B of the frame 105. The corners 110A, 110B may be integrated into the frame 105 on the respective lateral sides 170A, 170B (as illustrated) or implemented as separate components attached to the frame 105 on the respective sides 170A, 170B. Alternatively, the corners 110A, 110B may be integrated into temples 125A, 125B attached to the frame 105.

In another example, the eyewear device 100 shown in FIG. 2B may include two projectors, a left projector 150A (not shown) and a right projector 150B (shown as projector 150). The left optical assembly 180A may include a left display matrix 177A (not shown) or a left set of optical strips 155'A, 155'B, . . . 155'N (155 prime, A through N, not shown) which are configured to interact with light from the left projector 150A. Similarly, the right optical assembly 180B may include a right display matrix 177B (not shown) or a right set of optical strips 155"A, 155"B, . . . 155"N (155 double prime, A through N, not shown) which are configured to interact with light from the right projector 150B. In this example, the eyewear device 100 includes a left display and a right display.

FIG. 3 is a diagrammatic depiction of a three-dimensional scene 306, a left raw image 302A captured by a left visible-light camera 114A, and a right raw image 302B captured by a right visible-light camera 114B. The left field of view 111A may overlap, as shown, with the right field of view 111B. The overlapping field of view 304 represents that portion of the image captured by both cameras 114A, 114B. The term 'overlapping' when referring to field of view means the matrix of pixels in the generated raw images overlap by thirty percent (30%) or more. 'Substantially overlapping' means the matrix of pixels in the generated raw images—or in the infrared image of scene—overlap by fifty percent (50%) or more. As described herein, the two raw images 302A, 302B may be processed to include a timestamp, which allows the images to be displayed together as part of a three-dimensional projection.

For the capture of stereo images, as illustrated in FIG. 3, a pair of raw red, green, and blue (RGB) images are captured of a real scene 306 at a given moment in time—a left raw image 302A captured by the left camera 114A and right raw image 302B captured by the right camera 114B. When the pair of raw images 302A, 302B are processed (e.g., by the image processor 412), depth images are generated. The generated depth images may be viewed on an optical assembly 180A, 180B of an eyewear device, on another display (e.g., the image display 580 on a mobile device 401), or on a screen.

The generated depth images are in the three-dimensional space domain and can comprise a matrix of vertices on a three-dimensional location coordinate system that includes an X axis for horizontal position (e.g., length), a Y axis for vertical position (e.g., height), and a Z axis for depth (e.g., distance). Each vertex may include a color attribute (e.g., a red pixel light value, a green pixel light value, or a blue pixel light value); a position attribute (e.g., an X location coordinate, a Y location coordinate, and a Z location coordinate); a texture attribute; a reflectance attribute; or a combination thereof. The texture attribute quantifies the perceived texture of the depth image, such as the spatial arrangement of color or intensities in a region of vertices of the depth image.

In one example, the virtual guided fitness system 400 (FIG. 4) includes the eyewear device 100, which includes a frame 105 and a left temple 125A extending from a left lateral side 170A of the frame 105 and a right temple 125B extending from a right lateral side 170B of the frame 105. The eyewear device 100 may further include at least two visible-light cameras 114A, 114B having overlapping fields of view. In one example, the eyewear device 100 includes a left visible-light camera 114A with a left field of view 111A, as illustrated in FIG. 3. The left camera 114A is connected to the frame 105 or the left temple 125A to capture a left raw image 302A from the left side of scene 306. The eyewear device 100 further includes a right visible-light camera 114B with a right field of view 111B. The right camera 114B is connected to the frame 105 or the right temple 125B to capture a right raw image 302B from the right side of scene 306.

FIG. 4 is a functional block diagram of an example virtual guided fitness system 400 that includes an eyewear device 100), a mobile device 401, and a server system 498 connected via various networks 495 such as the Internet. As shown, the virtual guided fitness system 400 includes a low-power wireless connection 425 and a high-speed wireless connection 437 between the eyewear device 100 and the mobile device 401.

As shown in FIG. 4, the eyewear device 100 includes one or more visible-light cameras 114A, 114B that capture still images, video images, or both still and video images, as described herein. The cameras 114A, 114B may have a direct memory access (DMA) to high-speed circuitry 430 and function as a stereo camera. The cameras 114A, 114B may be used to capture initial-depth images that may be rendered into three-dimensional (3D) models that are texture-mapped images of a red, green, and blue (RGB) imaged scene. The device 100 may also include a depth sensor that uses infrared signals to estimate the position of objects relative to the device 100. The depth sensor in some examples includes one or more infrared emitter(s) and infrared camera(s) 410.

The eyewear device 100 further includes two image displays of each optical assembly 180A, 180B (one associated with the left side 170A and one associated with the right side 170B). The eyewear device 100 also includes an image display driver 442, an image processor 412, low-power circuitry 420, and high-speed circuitry 430. The image displays of each optical assembly 180A, 180B are for presenting images, including still images, video images, or still and video images. The image display driver 442 is coupled to the image displays of each optical assembly 180A, 180B in order to control the display of images.

The components shown in FIG. 4 for the eyewear device 100 are located on one or more circuit boards, for example a printed circuit board (PCB) or flexible printed circuit (FPC), located in the rims or temples. Alternatively, or additionally, the depicted components can be located in the corners, frames, hinges, or bridge of the eyewear device 100. Left and right visible-light cameras 114A, 114B can include digital camera elements such as a complementary metal-oxide-semiconductor (CMOS) image sensor, a charge-coupled device, a lens, or any other respective visible or light capturing elements that may be used to capture data, including still images or video of scenes with unknown objects.

As shown in FIG. 4, high-speed circuitry 430 includes a high-speed processor 432, a memory 434, and high-speed wireless circuitry 436. In the example, the image display driver 442 is coupled to the high-speed circuitry 430 and operated by the high-speed processor 432 in order to drive the left and right image displays of each optical assembly 180A, 180B. High-speed processor 432 may be any processor capable of managing high-speed communications and operation of any general computing system needed for eyewear device 100. High-speed processor 432 includes processing resources needed for managing high-speed data transfers on high-speed wireless connection 437 to a wireless local area network (WLAN) using high-speed wireless circuitry 436.

In some examples, the high-speed processor 432 executes an operating system such as a LINUX operating system or other such operating system of the eyewear device 100 and the operating system is stored in memory 434 for execution. In addition to any other responsibilities, the high-speed processor 432 executes a software architecture for the eyewear device 100 that is used to manage data transfers with high-speed wireless circuitry 436. In some examples, high-speed wireless circuitry 436 is configured to implement Institute of Electrical and Electronic Engineers (IEEE) 802.11 communication standards, also referred to herein as Wi-Fi. In other examples, other high-speed communications standards may be implemented by high-speed wireless circuitry 436.

The low-power circuitry 420 includes a low-power processor 422 and low-power wireless circuitry 424. The low-power wireless circuitry 424 and the high-speed wireless circuitry 436 of the eyewear device 100 can include short-range transceivers (Bluetooth™ or Bluetooth Low-Energy (BLE)) and wireless wide, local, or wide-area network transceivers (e.g., cellular or Wi-Fi). Mobile device 401, including the transceivers communicating via the low-power wireless connection 425 and the high-speed wireless connection 437, may be implemented using details of the architecture of the eyewear device 100, as can other elements of the network 495.

Memory 434 includes any storage device capable of storing various data and applications, including, among other things, camera data generated by the left and right visible-light cameras 114A, 114B, the infrared camera(s) 410, the image processor 412, and images generated for display by the image display driver 442 on the image display of each optical assembly 180A, 180B. Although the memory 434 is shown as integrated with high-speed circuitry 430, the memory 434 in other examples may be an independent, standalone element of the eyewear device 100. In certain such examples, electrical routing lines may provide a connection through a chip that includes the high-speed processor 432 from the image processor 412 or low-power processor 422 to the memory 434. In other examples, the high-speed processor 432 may manage addressing of memory 434 such that the low-power processor 422 will boot the high-speed processor 432 any time that a read or write operation involving memory 434 is needed.

As shown in FIG. 4, various elements of the eyewear device 100 can be coupled to the low-power circuitry 420, high-speed circuitry 430, or both. For example, the infrared camera 410 (including in some implementations an infrared emitter), the user input devices 491 (e.g., touchpad 181), the microphone(s) 139, and the inertial measurement unit (IMU) 472 may be coupled to the low-power circuitry 420, high-speed circuitry 430, or both.

Figure 5:
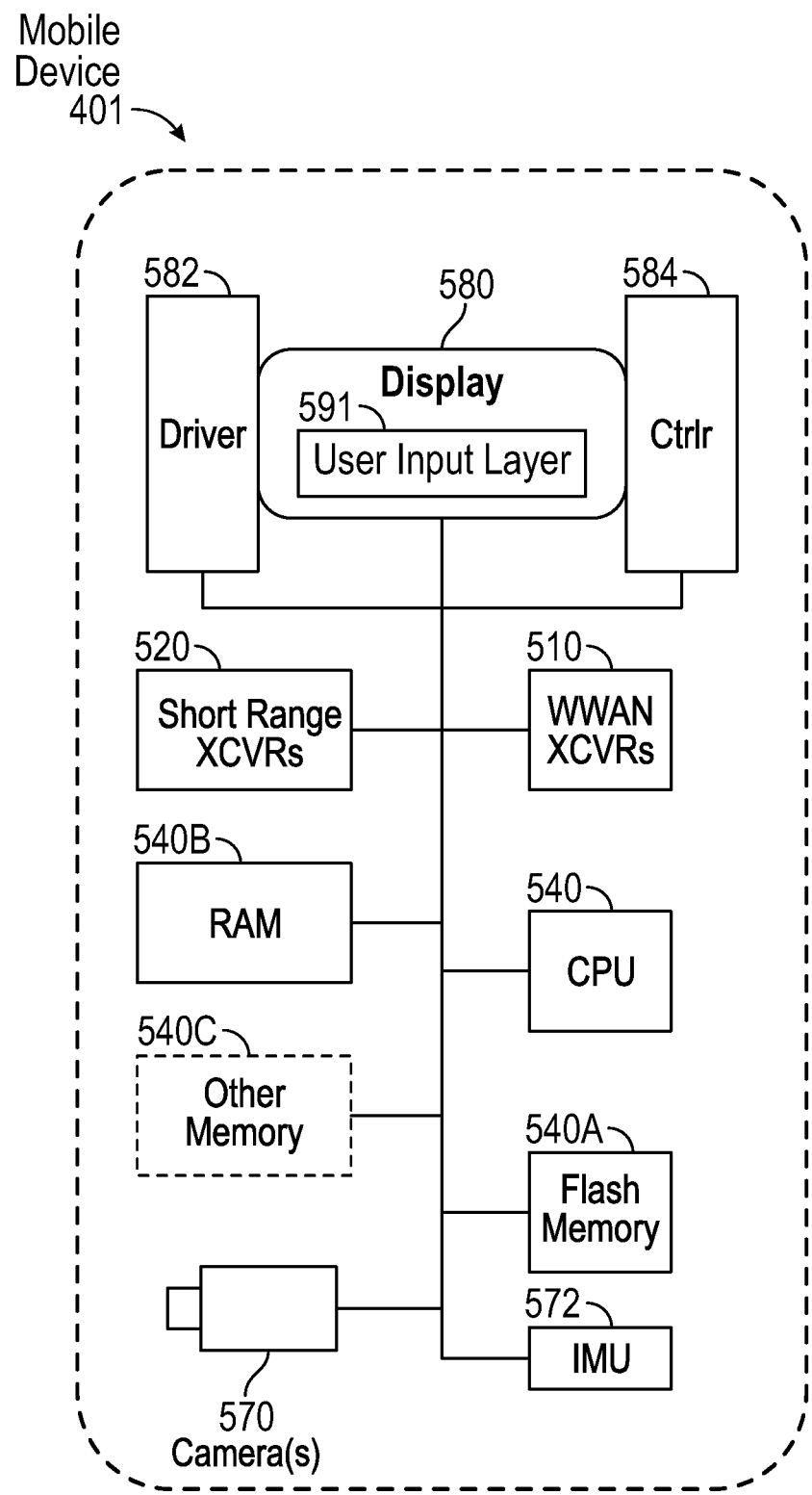
FIG. 5 is a diagrammatic representation of an example hardware configuration for a mobile device suitable for use in the example virtual guided fitness system of FIG. 4.

As shown in FIG. 5, the CPU 530 of the mobile device 401 may be coupled to a camera system 570, a mobile display driver 582, a user input layer 591, and a memory 540A.

The server system 498 may be one or more computing devices as part of a service or network computing system, for example, that include a processor, a memory, and network communication interface to communicate over the network 495 with an eyewear device 100 and a mobile device 401.

The output components of the eyewear device 100 include visual elements, such as the left and right image displays associated with each lens or optical assembly 180A, 180B as described in FIGS. 2A and 2B (e.g., a display such as a liquid crystal display (LCD), a plasma display panel (PDP), a light emitting diode (LED) display, a projector, or a waveguide). The eyewear device 100 may include a user-facing indicator (e.g., an LED, a loudspeaker 191, or a vibrating actuator), or an outward-facing signal (e.g., an LED, a loudspeaker 191). The image displays of each optical assembly 180A, 180B are driven by the image display driver 442. In some example configurations, the output components of the eyewear device 100 further include additional indicators such as audible elements (e.g., loudspeakers 191), tactile components (e.g., an actuator such as a vibratory motor to generate haptic feedback), and other signal generators. For example, the device 100 may include a user-facing set of indicators, and an outward-facing set of signals. The user-facing set of indicators are configured to be seen or otherwise sensed by the user of the device 100. For example, the device 100 may include an LED display positioned so the user can see it, one or more speakers 191 positioned to generate a sound the user can hear, or an actuator to provide haptic feedback the user can feel. The outward-facing set of signals are configured to be seen or otherwise sensed by an observer near the device 100. Similarly, the device 100 may include an LED, a loudspeaker 191, or an actuator that is configured and positioned to be sensed by an observer.

The input components of the eyewear device 100 may include alphanumeric input components (e.g., a touch screen or touchpad 181 configured to receive alphanumeric input, a photo-optical keyboard, or other alphanumeric-configured elements), pointer-based input components (e.g., a mouse, a touchpad 181, a trackball, a joystick, a motion sensor, or other pointing instruments), tactile input components (e.g., a button switch, a touch screen or touchpad 181 that senses the location, force or location and force of touches or touch gestures, or other tactile-configured elements), and audio input components (e.g., a microphone 139), and the like. The mobile device 401 and the server system 498 may include alphanumeric, pointer-based, tactile, audio, and other input components.

In some examples, the eyewear device 100 includes a collection of motion-sensing components referred to as an inertial measurement unit 472. The motion-sensing components may be micro-electro-mechanical systems (MEMS) with microscopic moving parts, often small enough to be part of a microchip. The inertial measurement unit (IMU) 472 in some example configurations includes an accelerometer, a gyroscope, and a magnetometer. The accelerometer senses the linear acceleration of the device 100 (including the acceleration due to gravity) relative to three orthogonal axes (x, y, z). The gyroscope senses the angular velocity of the device 100 about three axes of rotation (pitch, roll, yaw). Together, the accelerometer and gyroscope can provide position, orientation, and motion data about the device relative to six axes (x, y, z, pitch, roll, yaw). The magnetometer, if present, senses the heading of the device 100 relative to magnetic north. The position of the device 100 may be determined by location sensors, such as a GPS unit 473, one or more transceivers to generate relative position coordinates, altitude sensors or barometers, and other orientation sensors. Such positioning system coordinates can also be received over the wireless connections 425, 437 from the mobile device 401 via the low-power wireless circuitry 424 or the high-speed wireless circuitry 436.

The IMU 472 may include or cooperate with a digital motion processor or programming that gathers the raw data from the components and compute a number of useful values about the position, orientation, and motion of the device 100. For example, the acceleration data gathered from the accelerometer can be integrated to obtain the velocity relative to each axis (x, y, z); and integrated again to obtain the position of the device 100 (in linear coordinates, x, y, and z). The angular velocity data from the gyroscope can be integrated to obtain the position of the device 100 (in spherical coordinates). The programming for computing these useful values may be stored in memory 434 and executed by the high-speed processor 432 of the eyewear device 100.

The eyewear device 100 may optionally include additional peripheral sensors, such as biometric sensors, specialty sensors, or display elements integrated with eyewear device 100. For example, peripheral device elements may include any I/O components including output components, motion components, position components, or any other such elements described herein. For example, the biometric sensors may include components to detect expressions (e.g., hand expressions, facial expressions, vocal expressions, body gestures, or eye tracking), to measure bio signals (e.g., blood pressure, heart rate, body temperature, perspiration, or brain waves), or to identify a person (e.g., identification based on voice, retina, facial characteristics, fingerprints, or electrical bio signals such as electroencephalogram data), and the like.

The mobile device 401 may be a smartphone, tablet, laptop computer, access point, or any other such device capable of connecting with eyewear device 100 using both a low-power wireless connection 425 and a high-speed wireless connection 437. Mobile device 401 is connected to server system 498 and network 495. The network 495 may include any combination of wired and wireless connections.

The virtual guided fitness system 400, as shown in FIG. 4, includes a computing device, such as mobile device 401, coupled to an eyewear device 100 over a network. The virtual guided fitness system 400 includes a memory for storing instructions and a processor for executing the instructions. Execution of the instructions of the virtual guided fitness system 400 by the processor 432 configures the eyewear device 100 to cooperate with the mobile device 401. The virtual guided fitness system 400 may utilize the memory 434 of the eyewear device 100 or the memory elements 540A, 540B, 540C of the mobile device 401 (FIG. 5). Also, the virtual guided fitness system 400 may utilize the processor elements 432, 422 of the eyewear device 100 or the central processing unit (CPU) 530 of the mobile device 401 (FIG. 5). In addition, the virtual guided fitness system 400 may further utilize the memory and processor elements of the server system 498. In this aspect, the memory and processing functions of the virtual guided fitness system 400 can be shared or distributed across the processors and memories of the eyewear device 100, the mobile device 401, and the server system 498.

In some implementations, the memory 434 includes or is coupled to a guided fitness application 910, a localization system 915, an image processing system 920, a voice recognition module 925, and an avatar animation engine 930.

In a virtual guided fitness system 400 in which an inertial measurement unit (IMU) 472 is capturing frames of motion data 902, the guided fitness application 910 configures the processor 432 to detect motion (e.g., motion of the eyewear device 100 during calisthenics), retrieve exercise data 880 associated with the detected motion, and present a virtual fitness experience 700, as described herein. In some implementations, in which a camera is capturing frames of video data 900, the guided fitness application 910 configures the processor 432 to detect exercise apparatus 650 (e.g., weight machines, cardio equipment, mats, free weights), retrieve apparatus data 882 associated with the detected apparatus, and present a virtual fitness experience 700, as described herein.

The localization system 915 configures the processor 432 to obtain localization data for use in determining the position of the eyewear device 100 relative to the physical environment. The localization data may be derived from a series of images, an IMU 472, a GPS unit 473, or a combination thereof.

The image processing system 920 configures the processor 432 to present an avatar 710, and a variety of graphical elements 712, 750, 770, 780, 720, 731, 721, 711 on a display of an optical assembly 180A, 180B in cooperation with the image display driver 442 and the image processor 412.

The voice recognition module 925 configures the processor 432 to perceive human speech, convert the received speech into frames of audio data 905, identify an inquiry based on the audio data 905, and assemble a response that is correlated to be responsive to the identified inquiry.

The avatar animation engine 930 configures the processor 432 to render an avatar 710 as a still image or as a moving image (e.g., partially or fully animated), for presentation on a display of an optical assembly 180A, 180B in cooperation with the image display driver 442 and the image processor 412. The avatar 710 in some implementations is a cartoon-like character called a Bitmoji® which is rendered to appear three-dimensional. Predefined and configurable, Bitmoji® avatars are accessible over the network 495 and, in some implementations, are stored in the fitness library 484 described herein.

FIG. 5 is a high-level functional block diagram of an example mobile device 401. Mobile device 401 includes a flash memory 540A which stores programming to be executed by the CPU 530 to perform all or a subset of the functions described herein.

The mobile device 401 may include a camera 570 that comprises at least two visible-light cameras (first and second visible-light cameras with overlapping fields of view) or at least one visible-light camera and a depth sensor with substantially overlapping fields of view. Flash memory 540A may further include multiple images or video, which are generated via the camera 570.

As shown, the mobile device 401 includes an image display 580, a mobile display driver 582 to control the image display 580, and a display controller 584. In the example of FIG. 5, the image display 580 includes a user input layer 591 (e.g., a touchscreen) that is layered on top of or otherwise integrated into the screen used by the image display 580.

Examples of touchscreen-type mobile devices that may be used include (but are not limited to) a smart phone, a personal digital assistant (PDA), a tablet computer, a laptop computer, or other portable device. However, the structure and operation of the touchscreen-type devices is provided by way of example; the subject technology as described herein is not intended to be limited thereto. For purposes of this discussion, FIG. 5 therefore provides a block diagram illustration of the example mobile device 401 with a user interface that includes a touchscreen input layer 591 for receiving input (by touch, multi-touch, or gesture, and the like, by hand, stylus, or other tool) and an image display 580 for displaying content As shown in FIG. 5, the mobile device 401 includes at least one digital transceiver (XCVR) 510, shown as WWAN XCVRs, for digital wireless communications via a wide-area wireless mobile communication network. The mobile device 401 also includes additional digital or analog transceivers, such as short-range transceivers (XCVRs) 520 for short-range network communication, such as via NFC, VLC, DECT, ZigBee, Bluetooth™, or Wi-Fi. For example, short range XCVRs 520 may take the form of any available two-way wireless local area network (WLAN) transceiver of a type that is compatible with one or more standard protocols of communication implemented in wireless local area networks, such as one of the Wi-Fi standards under IEEE 802.11.

To generate location coordinates for positioning of the mobile device 401, the mobile device 401 can include a global positioning system (GPS) receiver. Alternatively, or additionally the mobile device 401 can utilize either or both the short range XCVRs 520 and WWAN XCVRs 510 for generating location coordinates for positioning. For example, cellular network, Wi-Fi, or Bluetooth™ based positioning systems can generate very accurate location coordinates, particularly when used in combination. Such location coordinates can be transmitted to the eyewear device over one or more network connections via XCVRs 510, 520.

The client device 401 in some examples includes a collection of motion-sensing components referred to as an inertial measurement unit (IMU) 572 for sensing the position, orientation, and motion of the client device 401. The motion-sensing components may be micro-electro-mechanical systems (MEMS) with microscopic moving parts, often small enough to be part of a microchip. The inertial measurement unit (IMU) 572 in some example configurations includes an accelerometer, a gyroscope, and a magnetometer. The accelerometer senses the linear acceleration of the client device 401 (including the acceleration due to gravity) relative to three orthogonal axes (x, y, z). The gyroscope senses the angular velocity of the client device 401 about three axes of rotation (pitch, roll, yaw). Together, the accelerometer and gyroscope can provide position, orientation, and motion data about the device relative to six axes (x, y, z, pitch, roll, yaw). The magnetometer, if present, senses the heading of the client device 401 relative to magnetic north.

The IMU 572 may include or cooperate with a digital motion processor or programming that gathers the raw data from the components and compute a number of useful values about the position, orientation, and motion of the client device 401. For example, the acceleration data gathered from the accelerometer can be integrated to obtain the velocity relative to each axis (x, y, z); and integrated again to obtain the position of the client device 401 (in linear coordinates, x, y, and z). The angular velocity data from the gyroscope can be integrated to obtain the position of the client device 401 (in spherical coordinates). The programming for computing these useful values may be stored in on or more memory elements 540A, 540B, 540C and executed by the CPU 540 of the client device 401.

The transceivers 510, 520 (i.e., the network communication interface) conforms to one or more of the various digital wireless communication standards utilized by modern mobile networks. Examples of WWAN transceivers 510 include (but are not limited to) transceivers configured to operate in accordance with Code Division Multiple Access (CDMA) and 3rd Generation Partnership Project (3GPP) network technologies including, for example and without limitation, 3GPP type 2 (or 3GPP2) and LTE, at times referred to as "4G." For example, the transceivers 510, 520 provide two-way wireless communication of information including digitized audio signals, still image and video signals, web page information for display as well as web-related inputs, and various types of mobile message communications to/from the mobile device 401.

The mobile device 401 further includes a microprocessor that functions as a central processing unit (CPU); shown as CPU 530 in FIG. 4. A processor is a circuit having elements structured and arranged to perform one or more processing functions, typically various data processing functions. Although discrete logic components could be used, the examples utilize components forming a programmable CPU. A microprocessor for example includes one or more integrated circuit (IC) chips incorporating the electronic elements to perform the functions of the CPU. The CPU 530, for example, may be based on any known or available microprocessor architecture, such as a Reduced Instruction Set Computing (RISC) using an ARM architecture, as commonly used today in mobile devices and other portable electronic devices. Of course, other arrangements of processor circuitry may be used to form the CPU 530 or processor hardware in smartphone, laptop computer, and tablet.

The CPU 530 serves as a programmable host controller for the mobile device 401 by configuring the mobile device 401 to perform various operations, for example, in accordance with instructions or programming executable by CPU 530. For example, such operations may include various general operations of the mobile device, as well as operations related to the programming for applications on the mobile device. Although a processor may be configured by use of hardwired logic, typical processors in mobile devices are general processing circuits configured by execution of programming.

The mobile device 401 includes a memory or storage system, for storing programming and data. In the example, the memory system may include a flash memory 540A, a random-access memory (RAM) 540B, and other memory components 540C, as needed. The RAM 540B serves as short-term storage for instructions and data being handled by the CPU 530, e.g., as a working data processing memory. The flash memory 540A typically provides longer-term storage.

Hence, in the example of mobile device 401, the flash memory 540A is used to store programming or instructions for execution by the CPU 530. Depending on the type of device, the mobile device 401 stores and runs a mobile operating system through which specific applications are executed. Examples of mobile operating systems include Google Android, Apple iOS (for iPhone or iPad devices), Windows Mobile, Amazon Fire OS, RIM BlackBerry OS, or the like.

The processor 432 within the eyewear device 100 may construct a map of the environment surrounding the eyewear device 100, determine a location of the eyewear device within the mapped environment, and determine a relative position of the eyewear device to one or more objects in the mapped environment. The processor 432 may construct the map and determine location and position information using a simultaneous localization and mapping (SLAM) algorithm applied to data received from one or more sensors. Sensor data includes images received from one or both of the cameras 114A, 114B, distance(s) received from a laser range finder, position information received from a GPS unit 473, motion and acceleration data received from an IMU 572, or a combination of data from such sensors, or from other sensors that provide data useful in determining positional information. In the context of augmented reality, a SLAM algorithm is used to construct and update a map of an environment, while simultaneously tracking and updating the location of a device (or a user) within the mapped environment. The mathematical solution can be approximated using various statistical methods, such as particle filters, Kalman filters, extended Kalman filters, and covariance intersection. In a system that includes a high-definition (HD) video camera that captures video at a high frame rate (e.g., thirty frames per second), the SLAM algorithm updates the map and the location of objects at least as frequently as the frame rate; in other words, calculating and updating the mapping and localization thirty times per second.

Sensor data includes image(s) received from one or both cameras 114A, 114B, distance(s) received from a laser range finder, position information received from a GPS unit 473, motion and acceleration data received from an IMU 472, or a combination of data from such sensors, or from other sensors that provide data useful in determining positional information.

Figure 6:
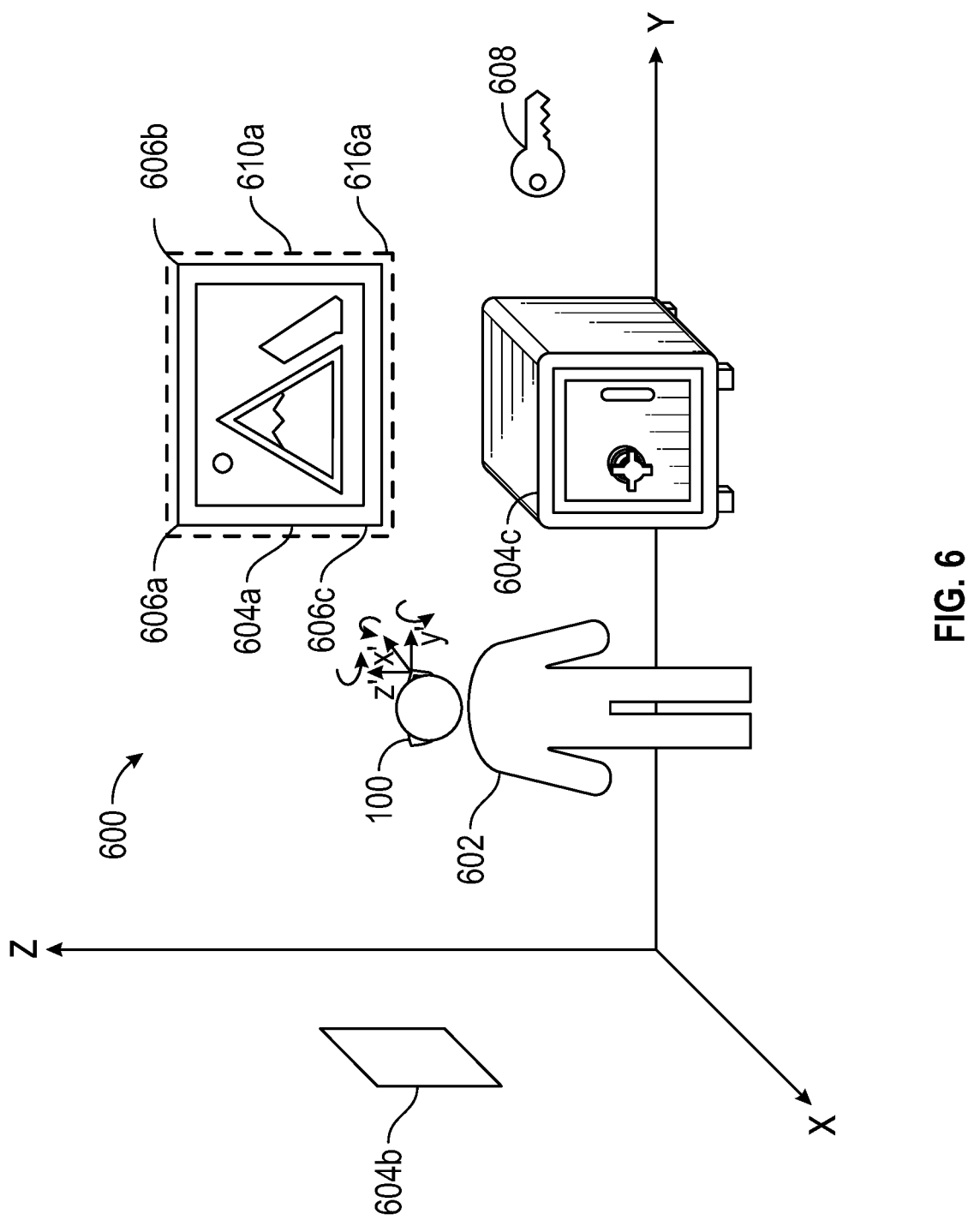
FIG. 6 is a schematic illustration of a user in an example environment for use in describing simultaneous localization and mapping.

FIG. 6 depicts an example physical environment 600 along with elements that are useful when using a SLAM application and other types of tracking applications (e.g., natural feature tracking (NFT)). A user 602 of eyewear device 100 is present in an example physical environment 600 (which, in FIG. 6, is an interior room). The processor 432 of the eyewear device 100 determines its position with respect to one or more objects 604 within the environment 600 using captured images, constructs a map of the environment 600 using a coordinate system (x, y, z) for the environment 600, and determines its position within the coordinate system. Additionally, the processor 432 determines a head pose (roll, pitch, and yaw) of the eyewear device 100 within the environment by using two or more location points (e.g., three location points 606a, 606b, and 606c) associated with a single object 604a, or by using one or more location points 606 associated with two or more objects 604a, 604b, 604c. The processor 432 of the eyewear device 100 may position a virtual object 608 (such as the key shown in FIG. 6) within the environment 600 for viewing during an augmented reality experience.

The localization system 915 in some examples a virtual marker 610a associated with a virtual object 608 in the environment 600. In augmented reality, markers are registered at locations in the environment to assist devices with the task of tracking and updating the location of users, devices, and objects (virtual and physical) in a mapped environment. Markers are sometimes registered to a high-contrast physical object, such as the relatively dark object, such as the framed picture 604a, mounted on a lighter-colored wall, to assist cameras and other sensors with the task of detecting the marker. The markers may be preassigned or may be assigned by the eyewear device 100 upon entering the environment.

Markers can be encoded with or otherwise linked to information. A marker might include position information, a physical code (such as a bar code or a QR code; either visible to the user or hidden), or a combination thereof. A set of data associated with the marker is stored in the memory 434 of the eyewear device 100. The set of data includes information about the marker 610a, the marker's position (location and orientation), one or more virtual objects, or a combination thereof. The marker position may include three-dimensional coordinates for one or more marker landmarks 616a, such as the corner of the generally rectangular marker 610a shown in FIG. 6. The marker location may be expressed relative to real-world geographic coordinates, a system of marker coordinates, a position of the eyewear device 100, or other coordinate system. The one or more virtual objects associated with the marker 610a may include any of a variety of material, including still images, video, audio, tactile feedback, executable applications, interactive user interfaces and experiences, and combinations or sequences of such material. Any type of content capable of being stored in a memory and retrieved when the marker 610a is encountered or associated with an assigned marker may be classified as a virtual object in this context. The key 608 shown in FIG. 6, for example, is a virtual object displayed as a still image, either 2D or 3D, at a marker location.

In one example, the marker 610a may be registered in memory as being located near and associated with a physical object 604a (e.g., the framed work of art shown in FIG. 6). In another example, the marker may be registered in memory as being a particular position with respect to the eyewear device 100.

Figure 11:
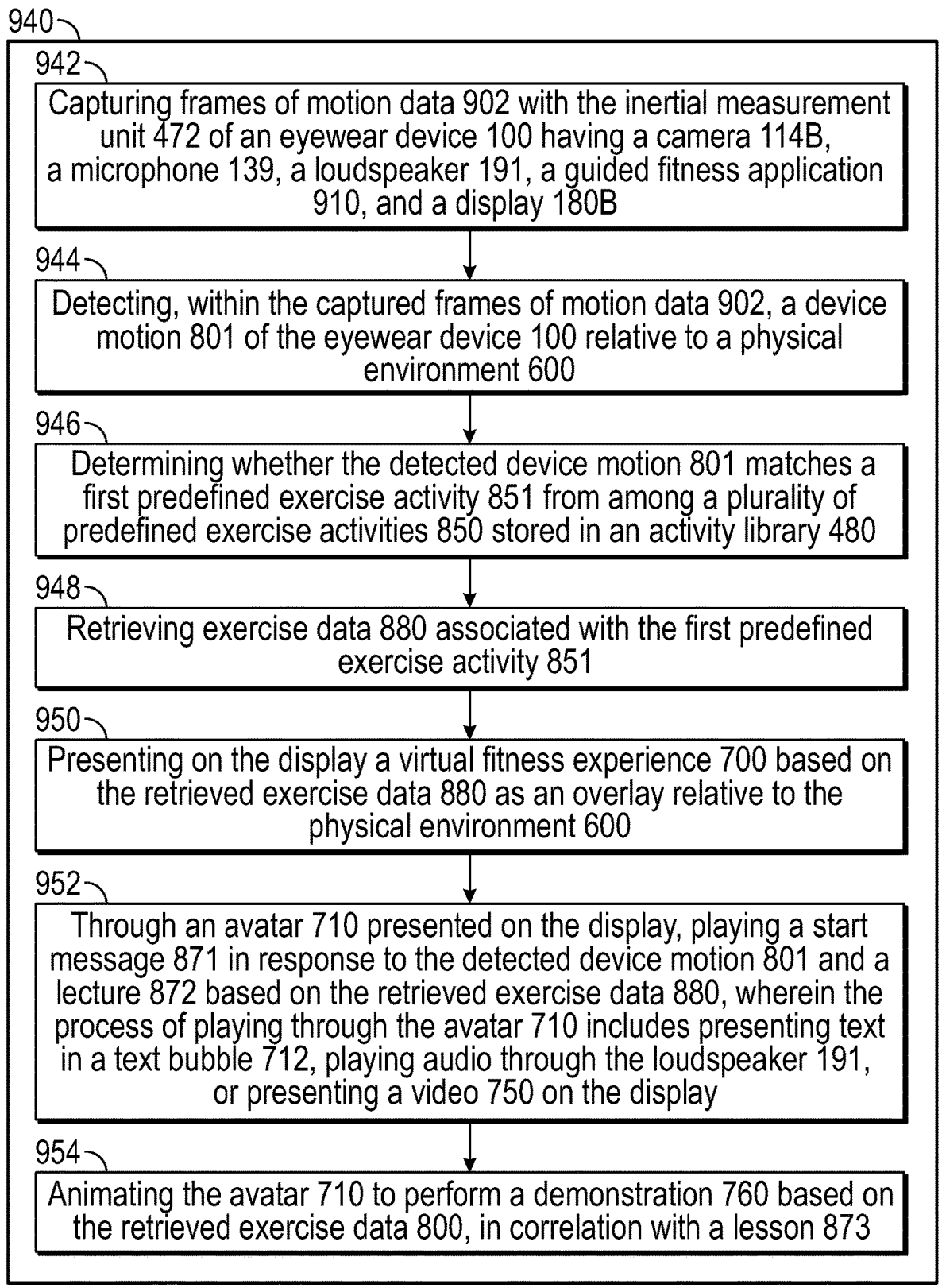
FIG. 11 is a flow chart listing the steps in an example method of presenting a virtual guided fitness experience on a display.

FIG. 11 is a flow chart 940 listing the steps in an example method of presenting a virtual fitness experience 700 on the display 180B of an eyewear device 100. Although the steps are described with reference to the eyewear device 100 described herein, other implementations of the steps described, for other types of devices, will be understood by one of skill in the art from the description herein. One or more of the steps shown and described may be performed simultaneously, in a series, in an order other than shown and described, or in conjunction with additional steps. Some steps may be omitted or, in some applications, repeated.

The guided fitness application 910 described herein, in some implementations, starts in response to receiving a selection through a user interface (e.g., selecting from a menu, pressing a button, using a touchpad) or through some other input means (e.g., hand gesture, finger motion, voice command). In other examples, the guided fitness application 910 starts in response to detecting a device motion 801 or detecting other motions, as described herein.

Block 942 in FIG. 11 describes an example step of capturing frames a motion data 902 with the IMU 472 of an eyewear device 100. The eyewear device 100 in this example includes an IMU 472, a camera 114B, a microphone 139, a loudspeaker 191, a guided fitness application 910, and a display 180B. In some implementations, the process of capturing frames of motion data 902 is ongoing during active use of the eyewear device 100. In other examples, the process of capturing starts in response to receiving a selection through a user interface or through some other input means. The example method, at block 942, in some implementations, includes storing the captured frames of motion data 902 in memory 434 on the eyewear device 100, at least temporarily, such that the frames are available for analysis.

Figure 7:
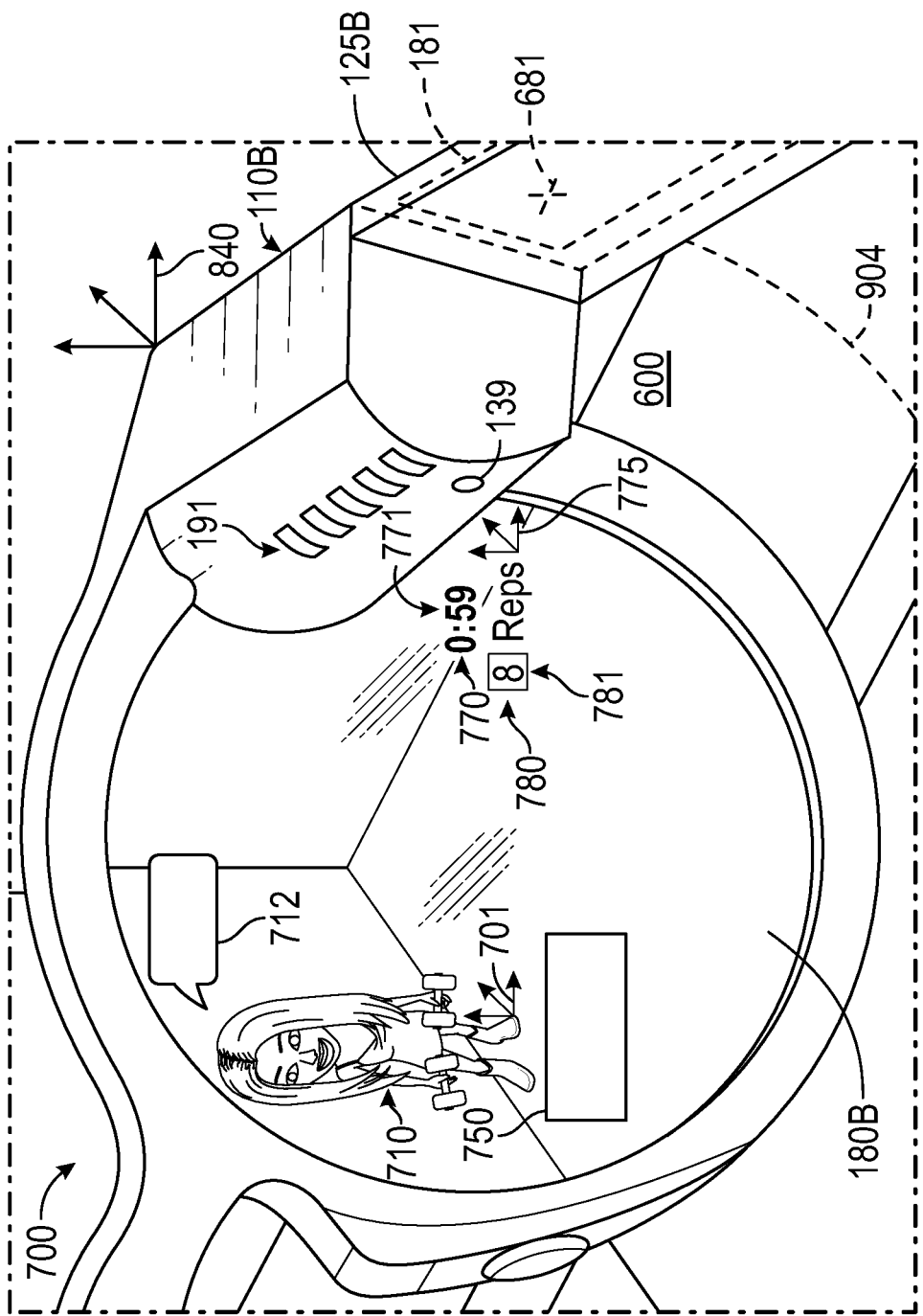
FIG. 7 is a perspective illustration of an example avatar and repetitions counter on a display.

Block 944 describes an example step of detecting a device motion 801 (e.g., motion of the eyewear device 100, typically supported by a wearer) in the captured frames of motion data 902. During operation and use by a wearer, the device motion 801 approximates the motion of the wearer. For example, when the wearer engages in calisthenics (e.g., jogging, jumping jacks, squats, push-ups), the device motion 801 registers and approximates the motion of the wearer. In some implementations, the IMU 472 is capable of capturing motion data at very high sample rates (e.g., 100 hertz (samples per second), 720 Hz, 1024 Hz, 1344 Hz, 3200 Hz, or higher). Frequent measurements facilitate the detection and analysis of relatively subtle device motion 801 over time. The process of detecting device motion 801 in some implementations includes detecting a current eyewear position 840 in three-dimensional coordinates relative to one or more elements of the physical environment 600, as shown in FIG. 7.

Block 946 in FIG. 11 describes the example step of determining whether the detected device motion 801 matches a first predefined exercise activity 851 (e.g., jogging, jumping jacks, squats, push-ups) from among a plurality of predefined exercise activities 850 stored in the activity library 480.

Any of a variety of predefined exercise activities 850 may be established, defined, and stored in the activity library 480. For example, the data record about one of the predefined exercise activities 850 includes a name or other identifier (e.g., squats), a series of expected values for starting, intermediate, and ending positions including three-dimensional coordinates, a series of expected accelerations relative to orthogonal axes (x, y, z), a series of expected angular velocities relative to three axes of rotation (pitch, roll, yaw), a point of view (e.g., side, top, bottom), a directional reference (e.g., vertical, horizontal), and other data and descriptors related to each exercise activity.

The process of determining whether the detected device motion 801 matches a first predefined exercise activity 851 includes comparing the frames of motion data 902 captured by the IMU 472 (e.g., position, acceleration, angular velocity) to the data stored about the predefined exercise activities 850 (e.g., position coordinates, expected accelerations, expected angular velocities).

As used herein, the term match is meant to include substantial matches or near matches, which may be governed by a predetermined confidence value associated with possible or candidate matches. The detected motion may include three-dimensional coordinates and other values, as found in the captured frames of motion data 902. In some examples, the matching process includes calculating the sum of the mathematical difference between the characteristics of a detected device motion 801 and the corresponding stored data values about each of the predefined exercise activities 850. In this aspect, a mathematical difference falls within a configurable threshold accuracy value represents a match.

Block 948 in FIG. 11 describes an example step of retrieving exercise data 880 associated with the first predefined exercise activity 851, in response to determining in block 946 that the detected device motion 801 matches the first predefined exercise activity 851. In some implementations, the process of retrieving exercise data 880 includes looking up the stored data about the first predefined exercise activity 851 in the activity library 480. In other implementations, the process of gathering information about the first predefined exercise activity 851 includes searching the internet. In this aspect, the process of retrieving exercise data 880 includes assembling search terms, executing a search, and harvesting information relevant to the first predefined exercise activity 851. The guided fitness application 910, in some implementations, is configured to access one or more preferred search engines, websites, and other internet-based resources. In some implementations, the process of retrieving exercise data 880 using an internet search involves using a machine-learning algorithm to select the search engine, web resources, and website data most likely to retrieve relevant container information quickly and efficiently.

Block 950 in FIG. 11 describes an example step of presenting a virtual fitness experience 700 on the display 180B as an overlay relative to the physical environment 600. The virtual fitness experience 700 is based on the retrieved exercise data 880 and presented in response to detecting the device motion 801.

FIG. 7 is a perspective illustration of several example elements of a virtual fitness experience 700, including an avatar 710, a repetitions counter 780, and a stopwatch 770.

In the example shown, the avatar 710 is presented on the display at an avatar position 701 relative to the display 180B. In some implementations, the avatar position 701 is defined in relation to the display 180B, such that the avatar 710 will be presented at a consistent position on the display (e.g., on the left side). Similarly, in this example, the repetitions counter 780 and the stopwatch 770 are presented on the display at an information position 775 relative to the display 180B, such that those elements will be presented at a consistent position on the display (e.g., on the right side).

As used herein, a repetition refers to and includes a training movement that is repeated, especially a single cycle or sequence of raising and lowering a weight (e.g., a dumbbell, a user's body weight). A repetition typically begins at a first position, includes movement to a second position, may include a pause, and then includes a returning movement back toward the first position. A repetition relative to parts of the body may involve flexion and extension, abduction and adduction, medial and lateral rotation, elevation and depression, pronation and supination, dorsiflexion and plantarflexion, inversion and eversion, opposition and reposition, protraction and retraction, circumduction through an angular distance, and the like.

Block 952 in FIG. 11 describes an example step of presenting or playing messages, lectures, and other content through the avatar 710, as part of the process of presenting the virtual fitness experience 700 on the display 180B. In some implementations, the process includes playing, through the avatar 710, a start message 871 in response to the detected device motion 801. For example, the start message 871 may include a greeting (e.g., Hello), a general message (e.g., Welcome to the virtual fitness experience), a motion-related message (e.g., I see you are doing squats), and the like.

As described herein, the process of presenting or playing "through the avatar 720" refers to and includes presenting text in a text bubble 712, playing audio through the loudspeaker 191, presenting a video 750, and combinations thereof.

In some implementations, the process at block 952 includes playing, through the avatar 710, a lecture 872, the content of which is based on the retrieved exercise data 880. For example, a lecture 872 may include general information (e.g., Squats work some of the largest muscles of the legs), guidance as to form (e.g., Keep your chest up and your back straight), encouragement (e.g., Nice job), and the like.

The lecture 872 in some implementations includes a closing message to be delivered at or near the conclusion of an exercise program, one of the sessions in the program, or combinations thereof. A closing message in the lecture 872, for example, may include the actual duration of the exercise program or session, the number of repetitions completed, the number of calories burned, any personal record or personal best reached, and the like.

Block 954 in FIG. 11 describes an example step of animating the avatar 710 so that it performs a demonstration 760 in correlation with a lesson 873. The content of the lesson 873 and the animated movements in the demonstration 760 are based on the retrieved exercise data 880.

The lesson 873 is delivered by presenting text in a text bubble 712, playing audio through the loudspeaker 191, presenting a video 750, and combinations thereof. The lesson 873 refers to and includes a speech directly correlated with the demonstration 760, which may or may not be part of the lecture 872.

The avatar 710 shown in FIG. 7 may be rendered and presented as a stationary figure. The demonstration 760 in some implementations includes animating the avatar 710, using the avatar animation engine 930, to perform a motion or exercise using proper form. For example, a demonstration 760 based on the retrieved exercise data 880 (e.g., squats) may include fully animating the avatar 710 so that the avatar character appears to move and perform all or part of the exercise (e.g., rendering the avatar 710 performing a squat), demonstrates a particular tip as to form (e.g., showing a side view of the avatar 710 with chest up and back straight), highlighting a muscle group (e.g., rendering the avatar 710 with highlighted areas around the leg muscles), and the like. In some implementations, the avatar animation engine 930 renders and presents the avatar 710 on the display performing the demonstration 760. In other implementations, the animated avatar 710 is presented on the display along with a complementary video 750 (e.g., a figure or real person engaged in similar activity) presented on the display.

The demonstration 760 is correlated with the lesson 873, so that the content of the lesson 873 approximately coincides with the content of the demonstration 760. For example, during a demonstration 760 about proper form (e.g., showing a side view of the avatar 710), the lesson 873 includes information about proper form (e.g., Keep your chest up and your back straight).

The example process steps described in the flow chart 940 in FIG. 11 include, of course, detecting and processing additional motions. For example, the example process steps refer to and include detecting a subsequent device motion, retrieving subsequent exercise data associated with the detected subsequent device motion, and presenting the virtual fitness experience based on the retrieved subsequent exercise data.

Figure 12:
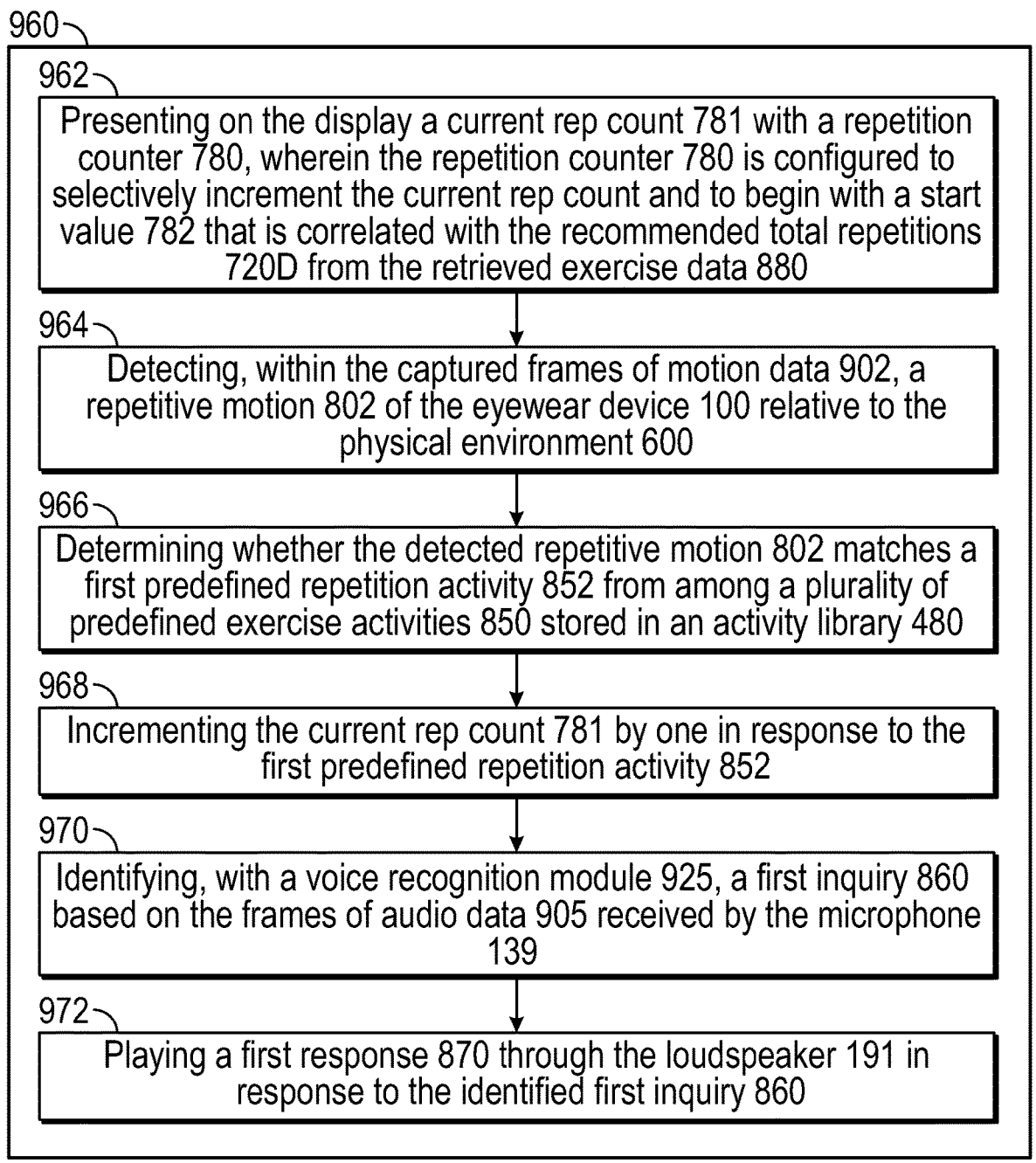
FIG. 12 is a flow chart listing the steps in an example method of presenting a selectively incremented repetition count on a display in response to detecting repetitive motions.

FIG. 12 is a flow chart 960 listing the steps in an example method of presenting a selectively incremented repetition count, as part of a virtual fitness experience 700 on the display 180B of an eyewear device 100. Although the steps are described with reference to the eyewear device 100 described herein, other implementations of the steps described, for other types of devices, will be understood by one of skill in the art from the description herein. One or more of the steps shown and described may be performed simultaneously, in a series, in an order other than shown and described, or in conjunction with additional steps. Some steps may be omitted or, in some applications, repeated.

Block 962 in FIG. 12 describes an example step of presenting on the display 180B a current rep count 781 (i.e., repetitions count) with a repetitions counter 780. As shown in FIG. 7, the repetitions counter 780 is presented at an information position 775 relative to the display 180B. In some implementations, the repetitions counter 780 is configured to selectively increment current rep count 781 (e.g., increase or decrease, if certain conditions are satisfied) and to begin with a start value 782 (e.g., zero) that is correlated with the retrieved exercise data 800. In this example, the retrieved exercise data 800 includes a recommended total number of repetitions 720D (e.g., twelve reps). The current rep count 781 may be configured to start at zero and incrementally increase by one until the recommended total repetitions 720D is performed. Some implementations presenting the recommended total repetitions 720D on the display.

Block 964 describes an example step of detecting a repetitive motion 802 (e.g., a squat motion, in which the eyewear device 100 moves from a starting location downward to a lower location, pauses, and returns in motion upward to the starting location) in the frames of motion data 902 captured by the IMU 472. High IMU sample rates facilitate the detection and analysis of repetitive motions 802 over time. The process of detecting a repetitive motion 802 in some implementations includes detecting the current eyewear position 840 in three-dimensional coordinates relative to one or more elements of the physical environment 600 over time.

Block 966 of FIG. 12 describes the example step of determining whether the detected repetitive motion 802 matches a first predefined repetition activity 852 (e.g., a squat rep) from among the plurality of predefined exercise activities 850 stored in the activity library 480. In this example, the data stored about the predefined exercise activities 850 includes data about the repetition activities associated with each exercise. For example, a data record about one of the predefined exercise activities 850 includes a name or other identifier (e.g., squats), a series of values associated with a single repetition, such as starting and ending coordinates, accelerations, velocities, and angular velocities.

The process of determining whether the detected repetitive motion 802 matches a first predefined repetition activity 852 includes comparing the frames of motion data 902 captured by the IMU 472 (e.g., position, acceleration, angular velocity) to the data stored about the repetition activity (e.g., positions, accelerations, velocities) associated with each of the predefined exercise activities 850.

Block 968 of FIG. 12 describes the example step of incrementing the current rep count 781 by one, in response to determining that the detected repetitive motion 802 matches the first predefined repetition activity 852. The process of incrementing is described herein as selective because the current rep count 781 is incremented only if the detected repetitive motion 802 matches the first predefined repetition activity 852. In some implementations, the process of incrementing the current rep count 781 includes presenting on the display the incremented current rep count.

In some implementations, the process of incrementing the current rep count 781 includes either increasing (e.g., counting up) or decreasing (e.g., counting down), and also includes first presenting the start value 782 on the display. For example, the start value 782 may be zero (e.g., in preparation for increasing the rep count 781 during a session) or the start value 782 may represent a maximum or goal value (e.g., in preparation for counting down from the goal value to zero during the session).

In a related aspect, the example display 180B shown in FIG. 7 includes a current time 771 presented on a stopwatch 770 that is presented on the display at a position that is adjacent, near, or otherwise relative to the information position 775. The retrieved exercise data 800, in some examples, includes a recommended duration. The recommend duration, in some implementations, is a time associated with the entire program or a time associated with each of one or more discrete sessions within the program, including rest periods. The stopwatch 770 may be configured to increment the current time 771 (e.g., increase or decrease) and to begin with a starting time (e.g., zero, thirty seconds) that is correlated with the recommended duration stored in the retrieved exercise data 800. The current time 771 may start at zero incrementally increase by one until the recommended duration is reached. In other implementations, the current time 771 may start at the recommend duration and incrementally decrease by one until zero is reached.

The process of incrementing the current time 771 may be started in response to the first detected device motion 801, the first detected repetitive motion 802, or some other event. In some implementations, the process of incrementing the current time 771 is configured to continue as long as the same device motion 801 (or the same repetitive motion 802) is detected and identified as a match. When a different or new device motion 801 (or a different repetitive motion 802) is detected and identified, the process of incrementing the current time 771 may be configured to re-start the current time 771 at a new starting time (e.g., zero, sixty seconds).

Block 970 of FIG. 12 describes an example step of identifying, with a voice recognition module 925, a first inquiry 860 based on frames of audio data 905 received by a microphone 139. The voice recognition module 925 is coupled to or otherwise accessible by the eyewear device 100. The process of identifying the first inquiry 860 includes receiving human speech through a microphone 139 and then converting the speech into frames of audio data 905. The voice recognition module 925 analyzes the frames of audio data 905, using automated speech recognition processing, to identify the contents of the first inquiry 860. In some implementations, the automated speech recognition involves using a machine-learning algorithm that has been trained to detect, decipher, and identify the contents of human speech quickly and efficiently.

Block 972 describes an example step of playing a first response 870 in response to the identified first inquiry 860. Like other messages and responses described herein, the first response 870 may be presented in text form (e.g., inside a speech bubble 712) or played audibly through the loudspeaker 191, or both. The process of assembling and playing the first response 870 by the voice recognition module 925 includes correlating the contents of the first response 870 with the contents of the first inquiry 860.

Blocks 970 and 972 of FIG. 12 describe an example process for conducting an interactive question-and-answer session with the avatar 710 in which the guided fitness application 910 provides responses that are correlated with and responsive to inquiries. This kind of voice-based interactive session, in some implementations, is active and available at any time and during any stage of the virtual fitness experience 700 described herein. For example, a voice-based interactive session of this kind may occur when the avatar 710 is first presented on the display, in response to a start message 871, during a lecture 872, during a demonstration 760 and lesson 730, during a video 750, when the current rep count 781 changes, when a program title 731 or session information appears on the display, when an exercise apparatus 650 is detected, when a repetitive apparatus motion 803 is detected, and at any other time during the guided virtual fitness experience 700.

In another aspect, the example step of detecting a repetitive motion 802 (e.g., a squat motion) at block 964 in some implementations includes presenting or playing messages, lectures, and other content through the avatar 710, as part of the process of presenting the virtual fitness experience 700. In some implementations, the process includes playing, through the avatar 710, a start message 871 in response to the detected repetitive motion 802. For example, the start message 871 may include a greeting, a general message (e.g., You last did twelve squats on Monday), a repetition-related message (e.g., Pause for two seconds before pressing upward), and the like.

In some implementations, the process includes playing, through the avatar 710, a lecture 872, the content of which is based on the retrieved exercise data 880—as well as the detected repetitive motion 802. For example, a lecture 872 may include general information (e.g., Let's do twelve squats today), guidance as to form (e.g., Head up), information about the current rep count 781 (e.g., That's ten reps), encouragement (e.g., Two more; you got this), and the like.

The process, in some implementations, includes animating the avatar 710 so that it performs a demonstration 760 in correlation with a lesson 873. The content of the lesson 873 and the animated movements in the demonstration 760 are based on the retrieved exercise data 880—as well as the detected repetitive motion 802. In this aspect, the detected repetitive motion 802 adds to the data accessible by the guided fitness application 910 to curate, update, improve, and deliver a customized virtual fitness experience 700.

The example process steps described in the flow chart 960 in FIG. 12 include, of course, detecting and processing additional repetitive motions. For example, the example process steps refer to and include detecting a subsequent repetitive motion, determining whether the detected subsequent repetitive motion matches a subsequent predefined repetition activity, and incrementing the current rep count by one in response to the subsequent predefined repetition activity.

Figure 8:
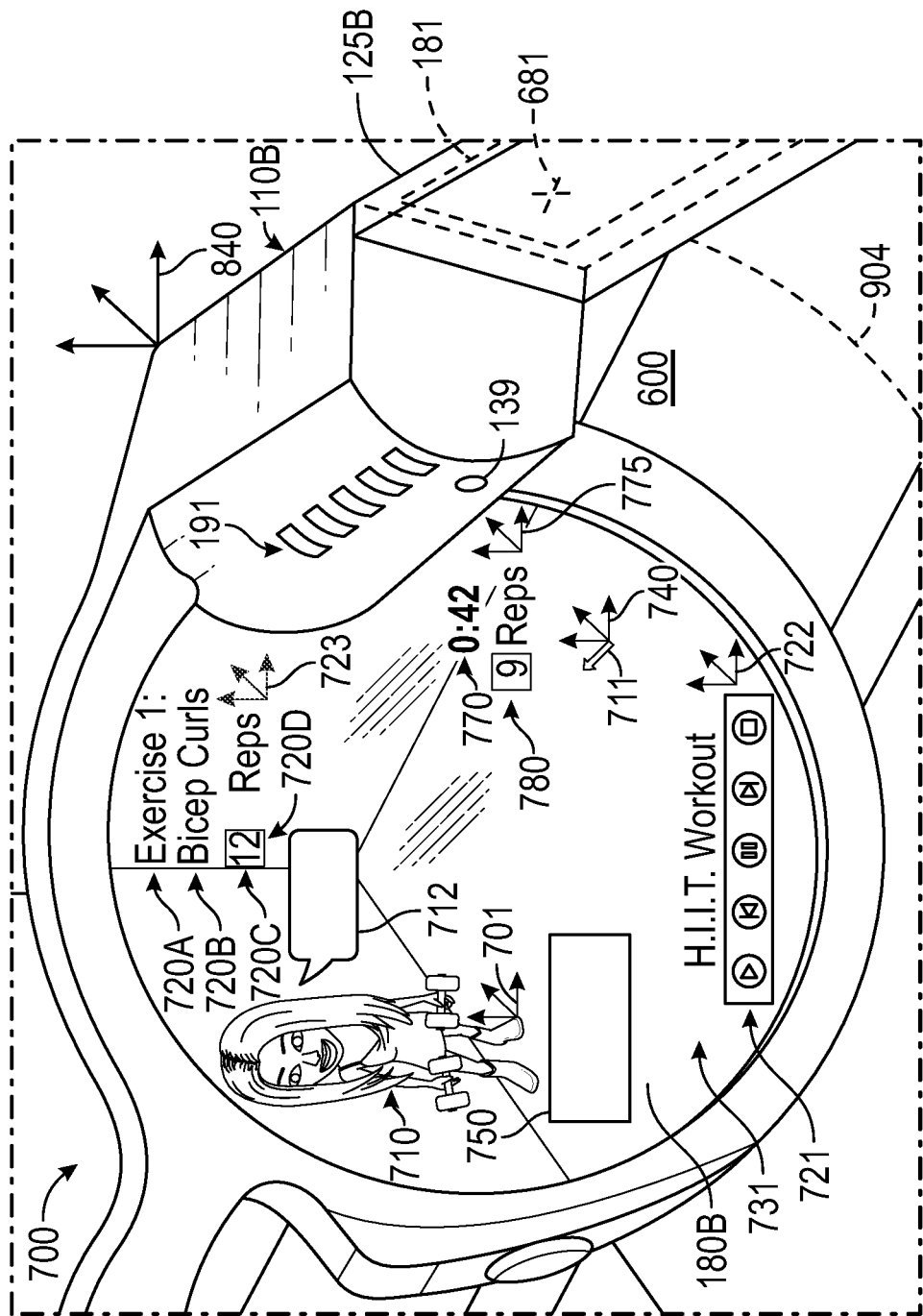
FIG. 8 is a perspective illustration of an example fitness program with session information and control elements presented on a display.

FIG. 8 is a perspective illustration of an example fitness program with session information and one or more graphical control elements 721 presented on a display 180B. In this example, the virtual fitness application 910 is configured to receive a program selection (e.g., through a graphical user interface, by voice command, or by other input means).

In response to receiving a program selection, the virtual fitness application 910 retrieves program data (e.g., from the fitness library 484, from the internet). The retrieved program data, in some implementations, includes a program title 731, one or more session titles 720A. Each session may include an activity name 720B, a recommended total number of repetitions 720D, and a recommended duration 720E.

As shown in FIG. 8, the virtual fitness application 910 is configured in this example to present on the display 180B, at a session position 723, the session title 720A (e.g., Exercise 1), the activity name 720B (e.g., Bicep Curls), and the recommended total of repetitions 720D (e.g., twelve). The session position 723 in this example is defined relative to the display 180B, so that it will be presented at consistent position on the display 180B (e.g., the center top).

The virtual fitness application 910 is configured in this example to present on the display 180B the program title 731 at a title position 722. The title position 722 in this example is defined relative to the display 180B, so that it will be presented at consistent position on the display 180B (e.g., the center bottom).

In some implementations, the virtual fitness application 910 is configured to present on the display a graphical control element 721 at a position on the display that is adjacent, near, or otherwise associated with the title position 722, as shown in FIG. 8.

As shown in FIG. 8, the example graphical control element 721 includes selectable buttons for play, go back, pause, skip forward, and stop. The components of graphical control element 721 may be selected using the touchpad 181 and a movable element 711, as described herein. The movable element 711 (e.g., a cursor, as shown in FIG. 8) is presented at a current element position 740 relative to the display. Interacting with the cursor 711, in some implementations, includes detecting a current fingertip location 681 relative to a touchpad 181 coupled to the eyewear device, as shown; and then presenting the cursor 711 at a current element position 740 on the display in accordance with the detected current fingertip location 681. In this example, a navigating action can be executed by moving the cursor 711 to one of the graphical elements on the display. For example, the selecting action includes placing the cursor 711 near a first control (e.g., one of the components of the graphical control element, such as a pause button). In some implementations, detecting a selecting action (e.g., achieved by placing the cursor 711 near the pause button and executing a tapping gesture) controls the progress of the guided fitness application 910 (e.g., by pausing until the pause button is selected again). The selecting action, in some implementations, includes receiving a voice command.

The graphical control element 721 may be configured to control the progress of the selected program, the session in progress, and other elements virtual guided fitness experience 700, including but not limited to the text bubble 712, the video 750, the message 871, the lecture 873, the demo 760 and its corresponding lesson 873.

In some implementations, the graphical control element 721 is configured to go back (and repeat portions) or skip forward (omit portions) of the virtual guided fitness experience 700. Additional or different graphical control elements 721 may be presented on the display and configured to perform other activities, such as record, save, share with a friend, delete, and any of a variety of other activities suitable for handling or processing an experience.

When operating based on a selected program, as illustrated in FIG. 8, the process in some implementations includes presenting an avatar 710 as described herein, as well as playing a message 871, a lecture 872, or a lesson 873 based on the retrieved program data (e.g., data stored in the fitness library 484 about an exercise program entitled "H.I.I.T Workout").

The process further includes animating the avatar 710 to perform a demonstration 760 that is correlated with a lesson 873, as described herein. For example, the retrieved program data may include one or more recorded animated demonstrations 760 and lesson 873 specifically curated, performed, and stored in association with a particular program.

When operating based on a selected program, as illustrated in FIG. 8, the process in some implementations includes presenting a current rep count 781 with a repetitions counter 780 and presenting a current time 771 with a stopwatch 700, as described herein.

Figure 13:
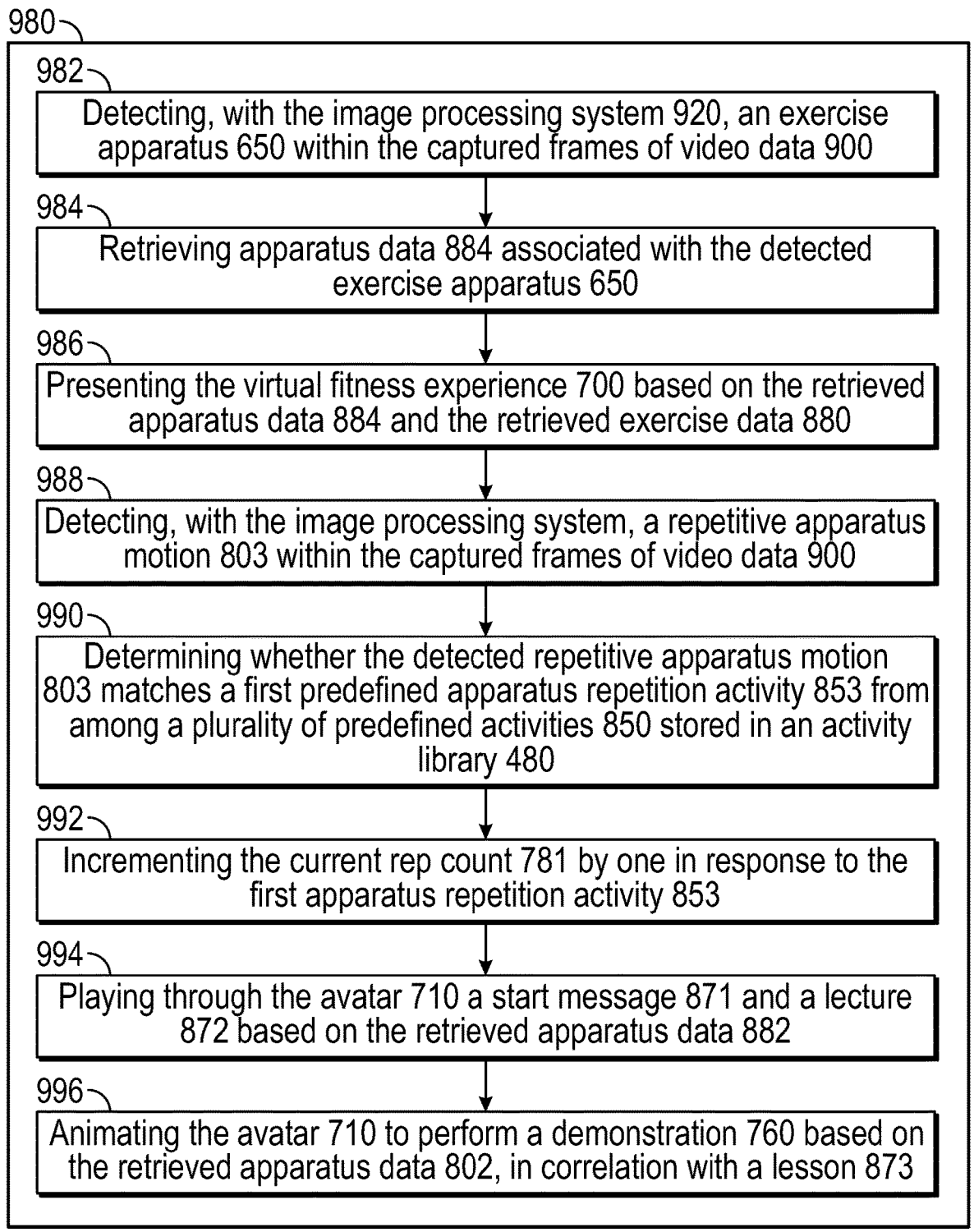
FIG. 13 is a flow chart listing the steps in an example method of detecting an exercise apparatus, detecting repetitive apparatus motion, and presenting a selectively incremented repetition count on a display.

FIG. 13 is a flow chart 980 listing the steps in an example method of detecting an exercise apparatus 650, detecting repetitive motion 803 of the exercise apparatus, and presenting a selectively incremented repetition count on a display 180B, as part of a virtual fitness experience 700. Although the steps are described with reference to the eyewear device 100 described herein, other implementations of the steps described, for other types of devices, will be understood by one of skill in the art from the description herein. One or more of the steps shown and described may be performed simultaneously, in a series, in an order other than shown and described, or in conjunction with additional steps. Some steps may be omitted or, in some applications, repeated.

Block 982 in FIG. 13 describes an example step of detecting an exercise apparatus 650 (e.g., a weight machine, a dumbbell or other free weight, a treadmill or other item of cardio equipment, a bench or mat) within the frames a video data 900 captured by the camera 114B of an eyewear device 100.

The eyewear device 100 in this example includes a camera 114B, an IMU 472, a microphone 139, a loudspeaker 191, a guided fitness application 910, and a display 180B. In some implementations, the eyewear device 100 includes one or more cameras 114A, 114B, as described herein, for capturing either still images or frames of video data 900. The eyewear device 100 in this example includes an image processing system 920 and one or more displays 180A, 180B. For example, as shown in FIG. 7, the eyewear device 100 includes a semi-transparent image display 180B which, as described herein, may include a semi-transparent lens layer and a display matrix layer configured to present images on the lens of the eyewear device. Graphical and virtual elements are presented on the display 180B as an overlay relative the surrounding physical environment 600. The effect, as shown, allows the viewer to see and interact with the presented contextual overlay 725 while the surrounding environment 600 also remains visible through the display 180B.

In some implementations, the high-speed processor 432 of the eyewear device 100 stores the captured frames of video data 900 with a camera 114B as the wearer moves through a physical environment 600. As described herein and shown in FIG. 7, the camera 114B typically has a camera field of view 904 that may capture images and video of the environment beyond the limits of the display 180B.

The camera system, in some implementations, includes one or more high-resolution, digital cameras equipped with a CMOS image sensor capable of capturing high-definition still images and high-definition video at relatively high frame rates (e.g., thirty frames per second or more). Each frame of digital video includes depth information for a plurality of pixels in the image. In this aspect, the camera system serves as a high-definition scanner by capturing a detailed input image of the physical environment. The camera system, in some implementations, includes a pair of high-resolution digital cameras 114A, 114B coupled to the eyewear device 100 and spaced apart to acquire a left-camera raw image and a right-camera raw image, as described herein. When combined, the raw images form an input image that includes a matrix of three-dimensional pixel locations. The example method, at block 982, in some implementations, includes storing the captured frames of video data 900 in memory 434 on the eyewear device 100, at least temporarily, such that the frames are available for analysis.

The process of capturing frames of video data 900 described herein, in some implementations, is ongoing during active use of the eyewear device 100. In other examples, the process of capturing starts in response to receiving a selection through a user interface (e.g., selecting from a menu, pressing a button) or through some other input means (e.g., hand gesture, voice command).

The example process of detecting an exercise apparatus 650, in some implementations, includes detecting a current apparatus position 705 (see FIG. 10) in three-dimensional coordinates relative to the display 180B or, alternatively, relative to another known position, such as the eyewear location 840. In some example implementations, the image processing system 920 analyzes the pixel-level data in the captured frames of video data 900 to determine whether the frame includes one or more exercise apparatuses 650.

Figure 9:
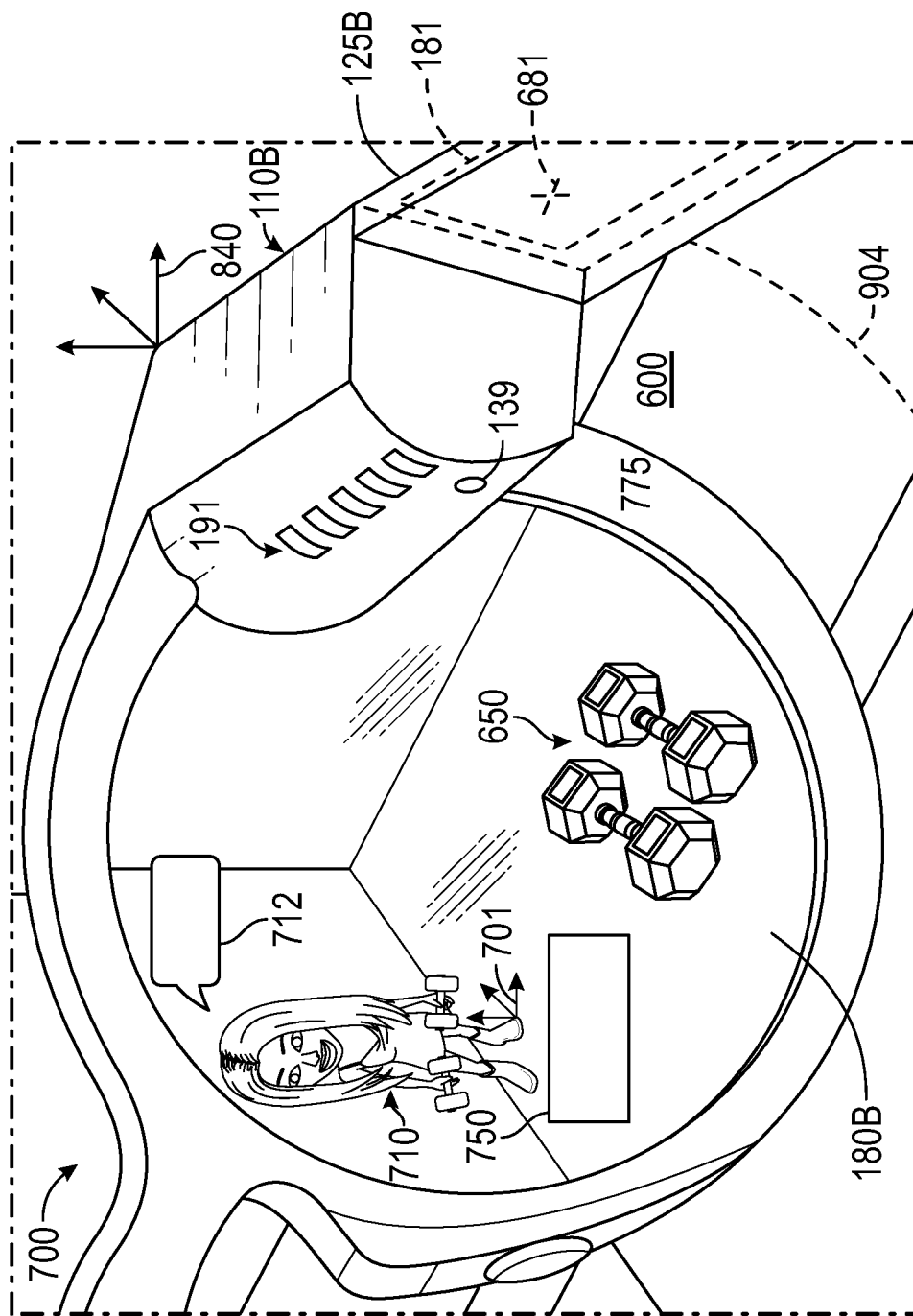
FIG. 9 is a perspective illustration of an example exercise apparatus detected by the system, along with an avatar presented on a display.

FIG. 9 is a perspective illustration of an example exercise apparatus 650 (e.g., a pair of dumbbells) in a physical environment 600. As shown, the avatar 710 is presented on the display at an avatar position 701 relative to the display 180B. As described herein, the process of presenting or playing "through the avatar 720" refers to and includes presenting text in a text bubble 712, playing audio through the loudspeaker 191, presenting a video 750, and combinations thereof.

Block 984 in FIG. 13 describes an example step of retrieving apparatus data 884 associated with the detected exercise apparatus 650 with the guided fitness application 910. The retrieved apparatus data 884 is stored in memory 434 on the eyewear device 100, at least temporarily. In some example implementations, the process of retrieving apparatus data 884 includes gathering information about the detected exercise apparatus 650 and its uses from one or more sources, including the activity library 480, object data library 482, and the fitness library 484; and may further include searching one or more websites on the internet. In this aspect, the process of retrieving apparatus data 884 includes assembling search terms, executing a search, and harvesting information relevant to the detected exercise apparatus 650 and its uses. The guided fitness application 910, in some implementations, is configured to access one or more preferred search engines, websites, and other internet-based resources. In some implementations, the process at block 946 of retrieving apparatus data 884 using an internet search involves using a machine-learning algorithm to select the search engine, web resources, and website data most likely to retrieve relevant container information quickly and efficiently.

The example process described at block 984 of FIG. 13 includes, of course, detecting and processing additional items of exercise apparatus 650. For example, the example process steps refer to and include detecting a subsequent exercise apparatus, retrieving subsequent apparatus data associated with the detected subsequent exercise apparatus, and including the subsequent apparatus data as part of the process of presenting the virtual fitness experience 700.

Block 986 in FIG. 13 describes an example step of presenting a virtual fitness experience 700 on the display 180B as an overlay relative to the physical environment 600. The virtual fitness experience 700 is based on the retrieved apparatus data 884 and the retrieved exercise data 880; and is presented in response to detecting the exercise apparatus 850.

Block 988 of FIG. 13 describes an example step of detecting a repetitive apparatus motion 803 (e.g., a bicep curl repetition, in which the detected barbell moves from a first location to a second location, pauses, and returns in motion to the first location) in the frames of image data 900 captured by the camera 114B. In some implementations, the visible-light cameras 114A, 114B described herein are capable of capturing high-definition (HD) video at a relatively high frame rate (e.g., thirty to sixty frames per second, or more). A high frame rate facilitates the detection and analysis of the motion of objects over time.

Figure 10:
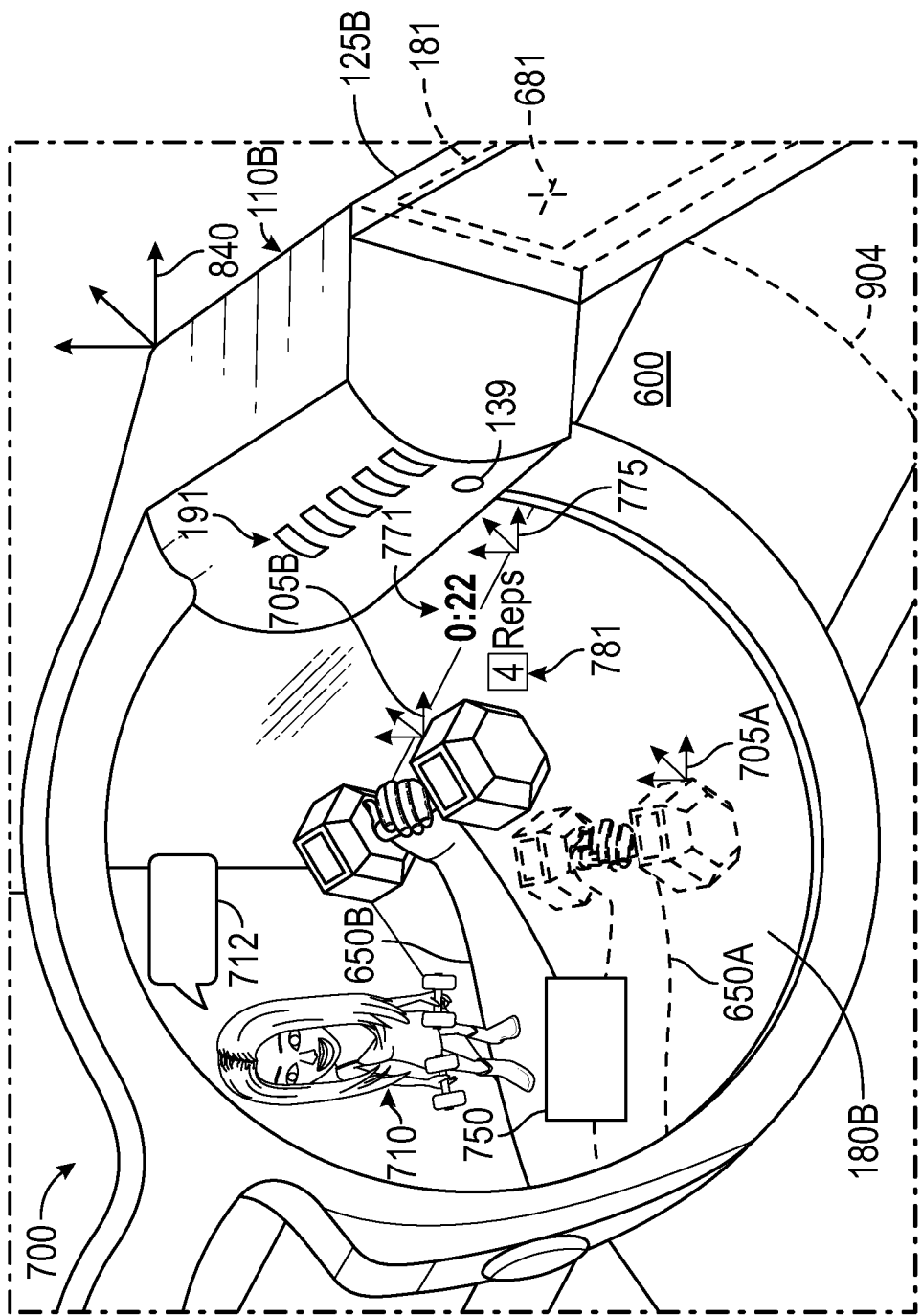
FIG. 10 is a perspective illustration of an example repetitive apparatus motion, an avatar, and a repetitions counter presented on a display.

The process of detecting a repetitive apparatus motion 803 in some implementations includes detecting a current apparatus position 705 over time and comparing it to previous apparatus positions. For example, FIG. 10 is a perspective illustration of an example repetitive apparatus motion 803; showing a detected exercise apparatus 650A at a first apparatus position 705A and the exercise apparatus 650B at a second apparatus position 705B. In some implementations, the image processing system 920 analyzes the pixel-level data in the captured frames of video data 900 to determine whether the frame includes a repetitive apparatus motion 803 (e.g., from position 705A to position 705B, and back again).

Those skilled in the art will understand that the process of detecting exercise apparatus 650 and current apparatus positions 705A, 705B occurs continually, over time, as the eyewear device 100 moves through the physical environment 600. Over time, additional exercise apparatus 650 may be detected within the field of view 904 of the camera 114B while others cease to be detected. Moreover, one or more detected exercise apparatus 650 may be moved to a new location in the physical environment 600 and then detected at a different or updated current apparatus position 705. In this aspect, the process of detecting is ongoing and substantially continuous, in which the image processing system 920 analyzes the pixel-level data in the captured frames of video data 900 to detect subsequent exercise apparatuses at subsequent apparatus positions.

In some implementations, the process at block 986 of presenting the virtual exercise experience 700 includes a supplemental process of presenting a contextual overlay (e.g., I see a pair of barbells. I recommend using ten-pound barbells) on the display 180B. The contextual overlay is based on the retrieved apparatus data 884 and may be presented by presenting text in a text bubble 712, playing audio through the loudspeaker 191, presenting a video 750, and combinations thereof. The contextual overlay may be presented at a position that is adjacent or otherwise associated with the detected exercise apparatus 650 (e.g., in a supplemental text bubble positioned on the display 180B so that it appears beside the location of the detected exercise apparatus 650. In some implementations, the contextual overlay is rendered in size and shape according to its contents, up to a configurable maximum size that will fit on the display 180B. In other implementations, the contents of the contextual overlay are limited in size according to the size and shape of the space available to present the contextual overlay.

As the eyewear device 100 moves through the physical environment 600, in some implementations, the contextual overlay will appear to remain near the current position of the exercise apparatus 650 using a process called localization. The localization system 915 on the eyewear device 100 in some implementations configures the processor 432 on the eyewear 100 to obtain localization data for use in determining the current eyewear location 840 relative to the current exercise apparatus position. The localization data may be derived from the captured frames of video data 900, an IMU unit 472, a GPS unit 473, or a combination thereof. The localization system 915 may construct a virtual map of various elements within the camera field of view 904 using a SLAM algorithm, as described herein, updating the map and the location of objects at least as frequently as the frame rate of the camera 114B (e.g., calculating and updating the mapping and localization of the current eyewear location 840 as frequently as thirty times per second, or more).

The process of localization in some implementations includes calculating a correlation between the detected exercise apparatus position and the current eyewear location 840. The term correlation refers to and includes one or more vectors, matrices, formulas, or other mathematical expressions sufficient to define the three-dimensional distance between the detected exercise apparatus position and the eyewear display 180B, in accordance with the current eyewear location 840. The current eyewear location 840, of course, is tied to or persistently associated with the display 180B which is supported by the frame of the eyewear device 100. In this aspect, the correlation performs the function of calibrating the motion of the eyewear 100 with the apparent motion of the detected container 650. Because the localization process occurs continually and frequently, the correlation is calculated continually and frequently, resulting in accurate and near real-time tracking of the detected current exercise apparatus position relative to the current eyewear location 840.

Because the localization process occurs continually and frequently, the correlation 950 is calculated continually and frequently, resulting in accurate and near real-time tracking of the current location of the exercise apparatus 650 relative to the current eyewear location 840.

Block 990 of FIG. 13 describes the example step of determining whether the detected repetitive apparatus motion 803 matches a first predefined apparatus repetition activity 853 (e.g., a barbell moving through a complete rep) from among the plurality of predefined exercise activities 850 stored in the activity library 480. In this example, the data stored about the predefined exercise activities 850 includes data about the repetition activities associated with each exercise. For example, a data record about one of the predefined exercise activities 850 includes a name or other identifier (e.g., bicep curls), one or more applicable exercise apparatuses 650 (e.g., one or two dumbbells, a straight barbell, a curling bar, a cable-based machine), and a series of values associated with a single repetition, such as starting and ending coordinates, accelerations, velocities, and angular velocities.

The process of determining whether the detected repetitive apparatus motion 803 matches a first predefined apparatus repetition activity 853 includes comparing the frames of image data 900 captured by the camera 114B to the data stored about the apparatus repetition activity (e.g., positions, accelerations, velocities) associated with each of the predefined exercise activities 850.

In some implementations, the matching process also includes comparing the frames of motion data 902 captured by the IMU 472 (e.g., position, acceleration, angular velocity) which describe the motion of the eyewear device 100—to the data stored about the apparatus repetition activity (e.g., positions, accelerations, velocities—associated with a body performing a repetition) associated with each of the predefined exercise activities 850. For example, the detected repetitive apparatus motion 803 (e.g., curling a single dumbbell) is also associated with a detected motion 801 of the body and the eyewear 100 (e.g., moving the head forward and backward, relatively slightly, during a single dumbbell curl). In this aspect, the image data 900 and motion data 902 may be correlated and analyzed together, to improve the detection and analysis of the detected repetitive apparatus motion 803.

Block 992 of FIG. 13 describes the example step of incrementing the current rep count 781 by one, in response to determining that the detected repetitive apparatus activity 803 matches the first predefined apparatus repetition activity 853. The process of incrementing is described herein as selective because the current rep count 781 is incremented only if the detected repetitive apparatus activity 803 matches the first predefined apparatus repetition activity 853. In some implementations, the process of incrementing the current rep count 781 includes presenting on the display the incremented current rep count.

Block 994 in FIG. 13 describes an example step of presenting or playing messages, lectures, and other content, as described herein, through the avatar 710, as part of the process of presenting the virtual fitness experience 700 on the display 180B. In some implementations, the process includes playing, through the avatar 710, a start message 871, a lecture 872, a lesson 873, and combinations thereof, in response to the detected exercise apparatus 650, the detected repetitive apparatus motion 803, the incremented rep count 781, and combinations thereof.

Block 996 in FIG. 13 describes an example step of animating the avatar 710 so that it performs a demonstration 760 in correlation with a lesson 873. The content of the lesson 873 and the animated movements in the demonstration 760 are based on the retrieved exercise data 880, the retrieved first predefined apparatus repetition activity 853, and combinations thereof.

The start message 871, a lecture 872, a lesson 873, and other information described herein is delivered by presenting text in a text bubble 712, playing audio through the loudspeaker 191, presenting a video 750, and combinations thereof.

The example process steps described in the flow chart 980 in FIG. 13 include, of course, detecting and processing additional repetitions. For example, the example process steps refer to and include detecting a subsequent apparatus motion, determining whether the subsequent apparatus motion matches a subsequent predefined apparatus repetition activity, and incrementing the current rep count by one in response to the subsequent predefined apparatus repetition activity.

Although the various systems and methods are described herein with reference to fitness, exercises, and exercise equipment, the technology described may be applied to detecting any type of experience or activity occurring in a physical environment, retrieving data about the detected activity, and presenting a virtual guided tutorial, lesson, training, teaching, or other guidance on a display.

Several of the processes described herein, in some implementations, involve the use of computer vision systems and machine-learning algorithms which are trained to analyze the pixel-level information contained in captured frames of video data 900. Machine-trained object-classification algorithms are used to identify objects detected in frames of video data 900 and, as the name implies, classify the objects as belonging to one or more discrete classes (e.g., free weights, exercise machines, weight benches, exercise mats, furniture). For example, classification algorithms may be used to facilitate the process of detecting an exercise apparatus 650 (as well as subsequent apparatuses).

Similarly, the processes of matching detected actions with one or more predefined activities, as described herein, in some implementations, involve the use of machine-trained algorithms for comparing the captured frames of motion data 902—and the captured frames of video data 900—to a plurality of predefined activities, with the goal of finding a match.

Also, the voice recognition processes described herein, in some implementations, involve the use of computer-based speech recognition systems (including natural language understanding (NLU) techniques) and machine-learning algorithms which are trained to analyze human speech, convert the speech to audio data, and assemble responses in context.

Machine learning refers to an algorithm that improves incrementally through experience. By processing a large number of different input datasets (e.g., photographs of various objects, containers, and activities in various environments), a machine-learning algorithm can develop improved generalizations about particular datasets, and then use those generalizations to produce an accurate output or solution when processing a new dataset. Broadly speaking, a machine-learning algorithm includes one or more parameters that will adjust or change in response to new experiences, thereby improving the algorithm incrementally; a process similar to learning.

In the context of computer vision, mathematical models attempt to emulate the tasks accomplished by the human visual system, with the goal of using computers to extract information from an image and achieve an accurate understanding of the contents of the image. Computer vision algorithms have been developed for a variety of fields, including artificial intelligence and autonomous navigation, to extract and analyze data in digital images and video.

Deep learning refers to a class of machine-learning methods that are based on or modeled after artificial neural networks. An artificial neural network is a computing system made up of a number of simple, highly interconnected processing elements (nodes), which process information by their dynamic state response to external inputs. A large artificial neural network might have hundreds or thousands of nodes.

A convolutional neural network (CNN) is a type of neural network that is frequently applied to analyzing visual images, including digital photographs and video. The connectivity pattern between nodes in a CNN is typically modeled after the organization of the human visual cortex, which includes individual neurons arranged to respond to overlapping regions in a visual field. A neural network that is suitable for use in the determining process described herein is based on one of the following architectures: VGG16, VGG19, ResNet50, Inception V3, Xception, or other CNN-compatible architectures.

In one example implementation, a trained item classification model receives a frame of video data which contains a detected item and abstracts the image in the frame into layers for analysis. Data in each layer is compared to items and objects stored in the object data library 482, layer by layer, based on the trained classification model, until a good match is identified.

In one example, the layer-by-layer image analysis is executed using a convolutional neural network. In a first convolution layer, the CNN identifies learned features (e.g., exercise equipment characteristics, product labels, exercise equipment descriptors, and the like). In a second convolution layer, the image is transformed into a plurality of images, in which the learned features are each accentuated in a respective sub-image. In a pooling layer, the sizes and resolution of the images and sub-images are reduced in order isolation portions of each image that include a possible feature of interest (e.g., a barbell, a jump rope, a container, a vessel). The values and comparisons of images from the non-output layers are used to classify the image in the frame.

Any of the functionality described herein for the eyewear device 100, the mobile device 401, and the server system 498 can be embodied in one or more computer software applications or sets of programming instructions, as described herein. According to some examples, "function," "functions," "application," "applications," "instruction," "instructions," or "programming" are program(s) that execute functions defined in the programs. Various programming languages can be employed to develop one or more of the applications, structured in a variety of manners, such as object-oriented programming languages (e.g., Objective-C, Java, or C++) or procedural programming languages (e.g., C or assembly language). In a specific example, a third-party application (e.g., an application developed using the ANDROID™ or IOS™ software development kit (SDK) by an entity other than the vendor of the particular platform) may include mobile software running on a mobile operating system such as IOS™, ANDROID™, WINDOWS® Phone, or another mobile operating system. In this example, the third-party application can invoke API calls provided by the operating system to facilitate functionality described herein.

Hence, a machine-readable medium may take many forms of tangible storage medium. Non-volatile storage media include, for example, optical or magnetic disks, such as any of the storage devices in any computer devices or the like, such as may be used to implement the client device, media gateway, transcoder, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code or data. Many of these forms of computer readable media may be involved in carrying one or more sequences of one or more instructions to a processor for execution.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as plus or minus ten percent from the stated amount or range.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A method of presenting a virtual fitness experience with an eyewear device, the eyewear device comprising a camera, an inertial measurement unit, a microphone, a loudspeaker, a guided fitness application, an image processing system, and a display, the method comprising:
   capturing frames of motion data with the inertial measurement unit;
   detecting a device motion of the eyewear device relative to a physical environment based on the captured frames of motion data;
   determining whether the detected device motion matches a first predefined exercise activity from among a plurality of predefined exercise activities stored in an activity library, wherein each predefined exercise activity is characterized by an exercise data record comprising at least one of an identifier, one or more positions, or one or more motions;
   retrieving a first exercise data record associated with the first predefined exercise activity; and
   presenting on the display a virtual fitness experience based on the retrieved first exercise data record as an overlay relative to the physical environment.

2. The method of claim 1, wherein the process of presenting a virtual fitness experience further comprises:
   presenting an avatar at an avatar position relative to the display;
   playing, through the avatar a start message associated with the retrieved first exercise data record;
   playing, through the avatar a lecture associated with the retrieved first exercise data record, wherein the process of playing through the avatar comprises one or more operations selected from the group consisting of presenting text in a text bubble playing audio through the loudspeaker and presenting a video on the display; and
   animating the avatar to perform a demonstration on the display adjacent the avatar position in correlation with a lesson wherein the demonstration is based on the retrieved first exercise data record.

3. The method of claim 2, further comprising:
   receiving a program selection;
   retrieving program data based on the received program selection the program data comprising a program title and one or more session titles, each including an activity name, a recommended total repetitions, and a recommended duration;
   presenting on the display at a session position the session title and a first activity name;
   presenting a current recommended total repetitions with a repetitions window positioned on the display adjacent the session position;
   presenting on the display the program title at a title position relative to the display;

playing, through the avatar a start message associated with the retrieved program data;

playing, through the avatar a lecture associated with the retrieved program data and animating the avatar to perform a demonstration on the display adjacent the avatar position in correlation with a lesson wherein the demonstration is based on the retrieved program data.

4. The method of claim 3, wherein the process of presenting a virtual fitness experience further comprises:

presenting on the display a graphical control element positioned adjacent the title position, the graphical control element comprising one or more controls selected from the group consisting of play, pause, back, next, and stop;

detecting a current fingertip location relative to a touchpad coupled to the eyewear device;

presenting a movable element at a current element position on the display in accordance with the detected current fingertip location;

identifying a first control of the graphical control element which is nearest to the current element position;

detecting a tapping gesture relative to the touchpad; and executing a selecting action relative to the first control in accordance with the detected tapping gesture.

5. The method of claim 1, further comprising:

detecting a subsequent device motion based on the captured frames of motion data;

retrieving a subsequent exercise data record associated with the detected subsequent device motion; and presenting the virtual fitness experience based on the retrieved subsequent exercise data record.

6. The method of claim 1, further comprising:

presenting on the display a current rep count with a repetition counter at an information position relative to the display, wherein the repetition counter is configured to selectively increment the current rep count and to begin with a start value that is correlated with the retrieved first exercise data record, which comprises a recommended total repetitions and a recommended duration;

detecting a repetitive motion of the eyewear device relative to the physical environment based on the captured frames of motion data;

determining whether the detected repetitive motion matches a first predefined repetition activity from among a plurality of predefined exercise activities stored in an activity library;

incrementing the current rep count by one in response to the first predefined repetition activity;

presenting a current time with a stopwatch positioned on the display adjacent the information position; and incrementing the current time by one unit during the recommended duration.

7. The method of claim 6, further comprising:

detecting a subsequent repetitive motion based on the captured frames of motion data;

determining whether the detected subsequent repetitive motion matches a subsequent predefined repetition activity; and incrementing the current rep count by one in response to the subsequent predefined repetition activity.

8. The method of claim 1, wherein the eyewear device further comprising a voice recognition module and wherein the method further comprises:

receiving human speech with the microphone;

converting the received speech into frames of audio data;

identifying, with the voice recognition module a first inquiry based on the frames of audio data; and playing a first response through the loudspeaker in response to the identified first inquiry.

9. The method of claim 1, further comprising:

capturing frames of video data within a field of view of the camera;

detecting, with the image processing system, an exercise apparatus within the captured frames of video data;

retrieving apparatus data associated with the detected exercise apparatus and presenting the virtual fitness experience based on the retrieved apparatus data and the retrieved first exercise data record.

10. The method of claim 9, wherein the process of presenting a virtual fitness experience further comprises:

presenting an avatar at an avatar position relative to the display;

playing, through the avatar a start message associated with the retrieved apparatus data;

playing, through the avatar a lecture associated with the retrieved apparatus data; and animating the avatar to perform a demonstration on the display adjacent the avatar position in correlation with a lesson wherein the demonstration is based on the retrieved apparatus data.

11. The method of claim 9, further comprising:

detecting, with the image processing system, a repetitive apparatus motion within the captured frames of video data;

determining whether the detected repetitive apparatus motion matches a first predefined apparatus repetition activity from among a plurality of predefined activities stored in an activity library; and incrementing a current rep count by one in response to the first apparatus repetition activity.

12. The method of claim 11, further comprising:

detecting a subsequent apparatus motion;

determining whether the subsequent apparatus motion matches a subsequent predefined apparatus repetition activity; and incrementing the current rep count by one in response to the subsequent predefined apparatus repetition activity.

13. A virtual guided fitness system, comprising:

an eyewear device comprising a camera, an inertial measurement unit, a microphone, a loudspeaker, a guided fitness application, an image processing system, and a display;

programming in a memory, wherein execution of the programming by a processor configures the eyewear device to perform functions, including functions to:

capture frames of motion data with the inertial measurement unit;

detect a device motion of the eyewear device relative to a physical environment based on the captured frames of motion data;

determine whether the detected device motion matches a first predefined exercise activity from among a plurality of predefined exercise activities stored in an activity library, wherein each predefined exercise activity is characterized by an exercise data record comprising at least one of an identifier, one or more positions, or one or more motions;

retrieve a first exercise data record associated with the first predefined exercise activity; and present on the display a virtual fitness experience based on the retrieved first exercise data record as an overlay relative to the physical environment.

14. The virtual guided fitness system of claim 13, wherein the function to present a virtual fitness experience further comprises functions to:
   present an avatar at an avatar position relative to the display;
   play, through the avatar a start message associated with the retrieved first exercise data record;
   play, through the avatar a lecture associated with the retrieved exercise data wherein the process of playing through the avatar comprises one or more operations selected from the group consisting of presenting text in a text bubble playing audio through the loudspeaker and presenting a video on the display; and
   animate the avatar using an avatar animation engine to perform a demonstration on the display adjacent the avatar position in correlation with a lesson wherein the demonstration is based on the retrieved first exercise data record.

15. The virtual guided fitness system of claim 13, wherein execution of the programming by the processor further configures the eyewear device to perform additional functions, including functions to:
   detect a subsequent device motion based on the captured frames of motion data;
   retrieve a subsequent exercise data record associated with the detected subsequent device motion;
   present the virtual fitness experience based on the retrieved subsequent exercise data record;
   present on the display a current rep count with a repetition counter at an information position relative to the display, wherein the repetition counter is configured to selectively increment the current rep count and to begin with a start value that is correlated with the retrieved subsequent exercise data record, which comprises a recommended total repetitions and a recommended duration;
   detect a repetitive motion of the eyewear device relative to the physical environment based on the captured frames of motion data;
   determine whether the detected repetitive motion matches a first predefined repetition activity from among a plurality of predefined exercise activities stored in an activity library;
   increment the current rep count by one in response to the first predefined repetition activity;
   present a current time with a stopwatch positioned on the display adjacent the information position;
   increment the current time by one unit during the recommended duration;
   detect a subsequent repetitive motion based on the captured frames of motion data;
   determine whether the detected subsequent repetitive motion matches a subsequent predefined repetition activity; and
   increment the current rep count by one in response to the subsequent predefined repetition activity.

16. The virtual guided fitness system of claim 15, wherein execution of the programming by the processor further configures the eyewear device to perform additional functions, including functions to:
   detect, with the image processing system, a repetitive apparatus motion within the captured frames of video data;
   determine whether the detected repetitive apparatus motion matches a first predefined apparatus repetition activity from among a plurality of predefined activities stored in an activity library;
   increment the current rep count by one in response to the first apparatus repetition activity;
   detect a subsequent apparatus motion;
   determine whether the subsequent apparatus motion matches a subsequent predefined apparatus repetition activity; and
   increment the current rep count by one in response to the subsequent predefined apparatus repetition activity.

17. A non-transitory computer-readable medium storing program code which, when executed, is operative to cause an electronic processor to perform the steps of:
   capturing frames of motion data with an inertial measurement unit of an eyewear device, the eyewear device further comprising a camera, a microphone, a loudspeaker, a guided fitness application, an image processing system, and a display;
   detecting a device motion of the eyewear device relative to a physical environment based on the captured frames of motion data;
   determining whether the detected device motion matches a first predefined exercise activity from among a plurality of predefined exercise activities stored in an activity library, wherein each predefined exercise activity is characterized by an exercise data record comprising at least one of an identifier, one or more positions, or one or more motions;
   retrieving a first exercise data record associated with the first predefined exercise activity;
   presenting on the display a virtual fitness experience based on the retrieved first exercise data record as an overlay relative to the physical environment wherein the step of presenting the virtual fitness experience further comprises:
   presenting an avatar at an avatar position relative to the display;
   playing, through the avatar a start message associated with the retrieved first exercise data record;
   playing, through the avatar a lecture associated with the retrieved first exercise data record, wherein the process of playing through the avatar comprises one or more operations selected from the group consisting of presenting text in a text bubble playing audio through the loudspeaker and presenting a video on the display; and
   animating the avatar to perform a demonstration on the display adjacent the avatar position in correlation with a lesson wherein the demonstration is based on the retrieved first exercise data record.

18. The non-transitory computer-readable medium storing program code of claim 17, wherein the step of presenting the virtual fitness experience further comprises:
   presenting on the display a current rep count with a repetition counter at an information position relative to the display, wherein the repetition counter is configured to selectively increment the current rep count and to begin with a start value that is correlated with the retrieved first exercise data record, which comprises a recommended total repetitions and a recommended duration;
   detecting a repetitive motion of the eyewear device relative to the physical environment based on the captured frames of the motion data;
   determining whether the detected repetitive motion matches a first predefined repetition activity from among a plurality of predefined exercise activities stored in an activity library;

incrementing the current rep count by one in response to the first predefined repetition activity;

presenting a current time with a stopwatch positioned on the display adjacent the information position; and incrementing the current time by one unit during the recommended duration.

19. The non-transitory computer-readable medium storing program code of claim 18, wherein the step of presenting the virtual fitness experience further comprises:

detecting, with the image processing system, a repetitive apparatus motion within the captured frames of video data;

determining whether the detected repetitive apparatus motion matches a first predefined apparatus repetition activity from among a plurality of predefined activities stored in an activity library; and incrementing the current rep count by one in response to the first apparatus repetition activity.

20. The non-transitory computer-readable medium storing program code of claim 17, wherein the step of presenting the virtual fitness experience further comprises:

capturing frames of video data within a field of view of the camera;

detecting, with the image processing system, an exercise apparatus within the captured frames of video data;

retrieving apparatus data associated with the detected exercise apparatus; and presenting the virtual fitness experience based on the retrieved apparatus data and the retrieved first exercise data record.

\* \* \* \* \*